(12) United States Patent
Burkholz et al.

(10) Patent No.: US 12,178,982 B2
(45) Date of Patent: Dec. 31, 2024

(54) INTRAVENOUS THERAPY SYSTEM FOR BLOOD VESSEL DETECTION AND VASCULAR ACCESS DEVICE PLACEMENT

(71) Applicant: Becton, Dickinson and Company, Franklin Lakes, NJ (US)

(72) Inventors: Jonathan Karl Burkholz, Salt Lake City, UT (US); Yiping Ma, Layton, UT (US); Joseph Spataro, Cottonwood Heights, UT (US); Huy Tran, Riverton, UT (US); Bart D. Peterson, Farmington, UT (US); Kathryn Willybiro, Park City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 584 days.

(21) Appl. No.: 16/742,676

(22) Filed: Jan. 14, 2020

(65) Prior Publication Data

US 2020/0230391 A1    Jul. 23, 2020

Related U.S. Application Data

(60) Provisional application No. 62/794,440, filed on Jan. 18, 2019.

(51) Int. Cl.
*A61M 39/02* (2006.01)
*A61B 8/00* (2006.01)
(Continued)

(52) U.S. Cl.
CPC ......... *A61M 39/0247* (2013.01); *A61B 8/085* (2013.01); *A61B 8/4455* (2013.01); *A61B 8/462* (2013.01); *A61B 17/3403* (2013.01); *A61B 34/20* (2016.02); *A61B 2017/3413* (2013.01); *A61B 2034/2051* (2016.02); (Continued)

(58) Field of Classification Search
CPC ....... A61B 8/085; A61B 8/4455; A61B 8/462; A61B 17/3403; A61B 34/20; A61B 2017/3413; A61B 2034/2051
See application file for complete search history.

(56) References Cited

U.S. PATENT DOCUMENTS 375,394 A * 12/1887 Strachan ................... E05D 1/04
 63/7
6,068,599 A   5/2000 Saito et al.
(Continued)

FOREIGN PATENT DOCUMENTS

EP    3308824      4/2018
JP    S61215961 A  9/1986
(Continued)

*Primary Examiner* — Amal Aly Farag
(74) *Attorney, Agent, or Firm* — Kirton McConkie; Whitney Blair; Kevin Stinger

(57) ABSTRACT

An intravenous therapy system, may include a processor; a data storage device; and a handheld ultrasound probe to detect structures within a patient's body, the handheld ultrasound probe including a video display device physically and operatively coupled to the handheld to display the structures within the patient's body and a magnetic field detector to detect the presence of a vascular access device (VAD) and provide closed-loop feedback to guide the VAD into a blood vessel within the patient's body detected by the ultrasound probe.

11 Claims, 11 Drawing Sheets

(51) Int. Cl.

| | |
|---|---|
| *A61B 8/08* | (2006.01) |
| *A61B 17/34* | (2006.01) |
| *A61B 34/20* | (2016.01) |
| *A61M 5/42* | (2006.01) |
| *A61M 25/01* | (2006.01) |

(52) U.S. Cl.
CPC ......... *A61M 5/427* (2013.01); *A61M 25/0113* (2013.01); *A61M 2039/0258* (2013.01); *A61M 2039/0291* (2013.01)

(56) References Cited

U.S. PATENT DOCUMENTS

| | | | |
|---|---|---|---|
| 7,214,191 B2 | 5/2007 | Stringer et al. | |
| 2007/0086633 A1* | 4/2007 | Boese | A61B 90/36 382/128 |
| 2008/0221396 A1* | 9/2008 | Garces | A61M 1/0286 600/300 |
| 2010/0010505 A1* | 1/2010 | Herlihy | A61B 90/11 600/585 |
| 2010/0016726 A1* | 1/2010 | Meier | A61B 8/0841 600/459 |
| 2011/0144658 A1 | 6/2011 | Wenderow et al. | |
| 2011/0166451 A1* | 7/2011 | Blaivas | A61B 8/467 600/439 |
| 2012/0259221 A1 | 10/2012 | Sheldon et al. | |
| 2013/0131501 A1 | 5/2013 | Blaivas et al. | |
| 2014/0323861 A1* | 10/2014 | Jin | H02J 7/0048 367/137 |
| 2015/0359991 A1 | 12/2015 | Dunbar et al. | |
| 2016/0210511 A1 | 7/2016 | Leong et al. | |
| 2016/0213398 A1 | 7/2016 | Liu | |
| 2017/0079549 A1 | 3/2017 | Henkel et al. | |
| 2017/0080166 A1 | 3/2017 | Bagwell et al. | |
| 2017/0203053 A1 | 7/2017 | Burkett | |
| 2017/0303889 A1* | 10/2017 | Grim | A61B 10/0283 |
| 2017/0347913 A1 | 12/2017 | Isaacson et al. | |
| 2018/0168740 A1* | 6/2018 | Ryan | A61B 90/36 |
| 2019/0374201 A1* | 12/2019 | Griffith | A61B 8/4483 |
| 2020/0069929 A1* | 3/2020 | Mason | A61M 1/3661 |

FOREIGN PATENT DOCUMENTS

| | | |
|---|---|---|
| JP | 2013078574 A | 5/2013 |
| JP | 2014221161 A | 11/2014 |
| KR | 20130089037 A | 8/2013 |
| KR | 20170093422 A | 8/2017 |
| WO | 2018/211235 | 4/2018 |
| WO | 2018112252 A1 | 6/2018 |
| WO | 20181122521 W | 6/2018 |

* cited by examiner

INTRAVENOUS THERAPY SYSTEM FOR BLOOD VESSEL DETECTION AND VASCULAR ACCESS DEVICE PLACEMENT

RELATED APPLICATIONS

This application claims the benefit of U.S. Provisional Application No. 62/794,440, filed Jan. 18, 2019, and entitled ULTRASOUND GUIDED, PORTABLE AUTOMATIC CATHETER PLACEMENT SYSTEM WITH ON-PROVE VISUAL DISPLAY, which is incorporated herein in its entirety.

BACKGROUND

Vascular access devices (VADs) are used for communicating fluid into the anatomy of a patient. For example, VADs, such as catheters, are commonly used for infusing fluid, such as saline solution, various medicaments, and/or total parenteral nutrition, into a patient, withdrawing blood from a patient, and/or monitoring various parameters of the patient's vascular system. Some catheters may also be used for withdrawing blood from the patient. To facilitate insertion into a body, the catheter may include a distal tip that includes a bevel used to interface with a skin of a patient as the bevel faces away from skin of the patient. During use of the catheter, the catheter is inserted at an angle relative to the skin of the patient and pierced through the skin of the patient. The catheter is to be passed into a vein of the patient so as to retrieve a blood sample or introduce a medicament or a plurality of medicaments.

VAD insertion into a vein, for example, has been difficult for phlebotomists, clinicians, and other health care providers (HCPs) at times because veins can be hard to see or palpate. Heat problems, dehydration, and age of the patient may all be some contributors to the inability to access any given patient's blood vessels. Ultrasound-based devices can identify those veins that within a patient and even as deep as 4-6 mm. However, ultrasound machines are expensive and bulky to use. Some ultrasound systems include a wired probe that is communicatively coupled to a larger visual display placed, at best, to the side of the patient the VAD is to be inserted into. These ultrasound systems require a clinician to hold and manipulate the ultrasound probe with one hand while placing the VAD with the second hand. This process is completed while the clinician is looking away from the VAD access point on the patient and at the off-site visual display device. The ability to effectively and properly insert the VAD in these scenarios is not intuitive and may lead to accidental damage to the patient's body tissues. Indeed, as a consequence of viewing the off-site video display, clinicians may be left to insert the catheter into subcutaneous layers of a patient's skin hoping to access a blood vessel. Such insertions, especially where a number of sequential insertions are attempted, may cause substantial pain, bruising, discomfort, and anxiety in patients to which the insertions are subjected to.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to vascular access devices (VADs) and related systems and methods. In some embodiments, an intravenous therapy system provides for the detection of blood vessels within a patient. The intravenous therapy system may include a handheld ultrasound probe to detect structures within a patient's body. Among other structures, the structures to be detected by the intravenous therapy system include veins into which certain medicaments may be introduced or blood samples may be retrieved. In order to help access the veins, the handheld ultrasound probe may include a video display physically coupled to, for example, a housing of the handheld ultrasound probe. The video display may provide, in the embodiments presented herein, a transverse plane view of the structures (e.g., a vein) within the patient's body. In an embodiment described herein, the video display may provide a coronal plane view of the structures (e.g., a vein) within the patient's body.

In some embodiments, the handheld ultrasound probe of the intravenous therapy system may include a magnetic field detector to determine the position of a needle tip of a needle and provide magnetic needle guidance. The magnetic field detector may detect the presence of the VAD, which may include the needle, which may be magnetizable. In some embodiments, the magnetic field detector may relay to the video display device data descriptive of the placement of the VAD relative to the patient's body. In some embodiments, this data may describe images to be superimposed over an ultrasound image produced by data received from the handheld ultrasound probe. In this manner, a clinician or other HCP may direct their view concurrently to the access point of the VAD at the patient's body and the video display to direct the insertion of the VAD though concurrent, real-time, display of data from the handheld ultrasound probe and the magnetic field detector.

In some embodiments, the intravenous therapy system may further include a feedback device used to indicate to a clinician or other health care provider (HCP) that the insertion of the VAD into the patient's body is incorrect. As described herein, the handheld ultrasound probe includes both an ultrasonic probe and the magnetic field detector to determine a location of the VAD relative to a structure within the patient's body such as a vein. A processor of the intravenous therapy system (either external or internal to the handheld ultrasound probe) may provide real-time feedback indicating whether the needle tip of the needle of the VAD is going to intersect with a selected or chosen structure such as the patient's vein. The feedback device may include a visual indicator such as a light or image on the handheld ultrasound probe, a speaker to provide audio feedback, a haptic device to provide haptic feedback or a combination thereof. In the embodiments presented herein, the video display device, speaker device, or haptic device may provide specific feedback that indicates whether the needle of the VAD is on a trajectory to intersect with a patient's vein as well as if and when the VAD has intersected with the target blood vessel. Additionally, a different visual, audible or haptic feedback signal may be provided by the feedback device if the needle of the VAD device's trajectory indicates it will not intersect the targeted vessel.

In some embodiments, the handheld ultrasound probe may include an automatic VAD advancement system. The VAD advancement system may include, in some embodiments, a port to place a selected VAD into. The VAD advancement system may register the placement of the VAD and, when the trajectory is determined, initiate one or more drive mechanisms or motors that cause the VAD to be inserted into a patient's body at a trajectory that will intercept with a blood vessel (i.e., a vein) of the patient. This automatic process of insertion of the VAD may include initiating feedback from the feedback devices described herein in order to direct the clinician or other HCP to hold the handheld ultrasound probe thereby maintaining a specific trajectory of the VAD.

In some embodiments, the motors may include linear and/or rotational motors. In some embodiments, the motors may facilitate distal advancement of a catheter of the VAD and the needle and/or proximal retraction of the needle. In some embodiments, the motors may facilitate angle adjustments or pivoting of the VAD to ensure the needle and the catheter are properly aligned to insert with the vein when the catheter and the needle are advanced distally.

In an embodiment, in order to initiate the distal advancement of the VAD automatically, the intravenous therapy system may include a button that a clinician may selectively actuate to cause the VAD to be inserted or advanced into the patient's body when a projected path of the needle intersects with the vein that is targeted. In some embodiments, when the intersection condition does not exist (i.e. the projected path of the needle does not intersect with the vein that is targeted), the distal advancement of the catheter and the needle may not start. In some embodiments, the distal advancement of the catheter and the needle may stop if the intersection condition no longer exists due to excessive movement of the patient or the handheld ultrasound probe.

In some embodiments, the handheld ultrasound probe may include a VAD recommendation module that provides feedback via, for example the display device, as to which of a plurality of different kinds of VADs to use to access the blood vessel of the patient. In an embodiment, the recommendation as to which VAD to use may be a verbal indication provided via audio output by a speaker of the handheld ultrasound probe. In some embodiments, the recommendation as to which VAD to use may include a type, size, length, or particular gauge of needle or catheter.

In the present specification and in the appended claims the term vascular access device (VAD) may be any tubing inserted into a blood vessel (e.g., vein or artery) used to administer fluids into a patient's bloodstream, monitor pressures, or collect a blood sample from the patient. VADs may include a peripheral intravenous device and a central venous access device among others. During operation of the handheld ultrasound probe of the intravenous therapy systems described herein, the VAD recommendation module may be executed to describe on the display device of the handheld ultrasound probe which VAD to use. In some embodiments, the VAD recommendation module may recommend a VAD having a needle and a catheter. In this specific embodiment, the automatic VAD advancement system may automatically separate the needle from the catheter when the intravenous therapy system has determined that the VAD has reached the target blood vessel. In this embodiment, the automatic VAD advancement system may be angled lower during the separation of the needle and catheter in order to properly and painlessly separate the needle from the catheter while the VAD is in the patient's body.

In some embodiments, the handheld ultrasound probe may be communicatively coupled to a data storage device that stores a mapping of blood vessels within the patient's body. In an embodiment, the data storage device forms part of the handheld ultrasound probe and is communicatively coupled to a processor also housed within the handheld ultrasound probe. This allows the handheld ultrasound probe to process data received by the handheld ultrasound probe and the magnetic field detector in order to provide data, some data presented in the form of images, at the video display device.

The video display device may present to the clinician or other HCP a view of the structures within the patient's body. In specific embodiments, the structures detected by the handheld ultrasound probe may be blood vessels such as veins and arteries. In some embodiments presented herein, the handheld ultrasound probe may detect the location of a vein based on an expected location of the vein, the movement of blood within the vein, and user selected indications of the vein. The video display may, in some embodiments, provide a transverse planar view of the blood vessel, a coronal planar view of the blood vessel, or a combination thereof.

In an embodiment, the video display device may include a touchscreen device used to receive input from a clinician or other HCP. In this embodiment, the handheld ultrasound probe, at the touchscreen device may receive input from the clinician indicating a location of a blood vessel presented in any view on the video display device. The processor of the handheld ultrasound probe may receive this input and determine a trajectory for the VAD to follow in order to cause the VAD to access the blood vessel. In these embodiments, the processor may, in real-time, provide feedback to a clinician or other HCP as to whether the trajectory of the VAD into the patient's body is an intersecting trajectory that will result in the VAD intersecting with the targeted blood vessel. In an embodiment, the trajectory of the VAD may be controlled automatically by the handheld ultrasound probe via the motors based on a continuous data feed from the magnetic field detectors and ultrasound probe. In an embodiment, feedback may be provided to the clinician or other HCP indicating a poor or sufficient trajectory when the VAD is manually inserted into the patient's body. This feedback may be provided to the clinician or other HCP audibly from an audio device, visually from the video display device, haptic feedback from a haptic device within the handheld ultrasound probe, or a combination thereof.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
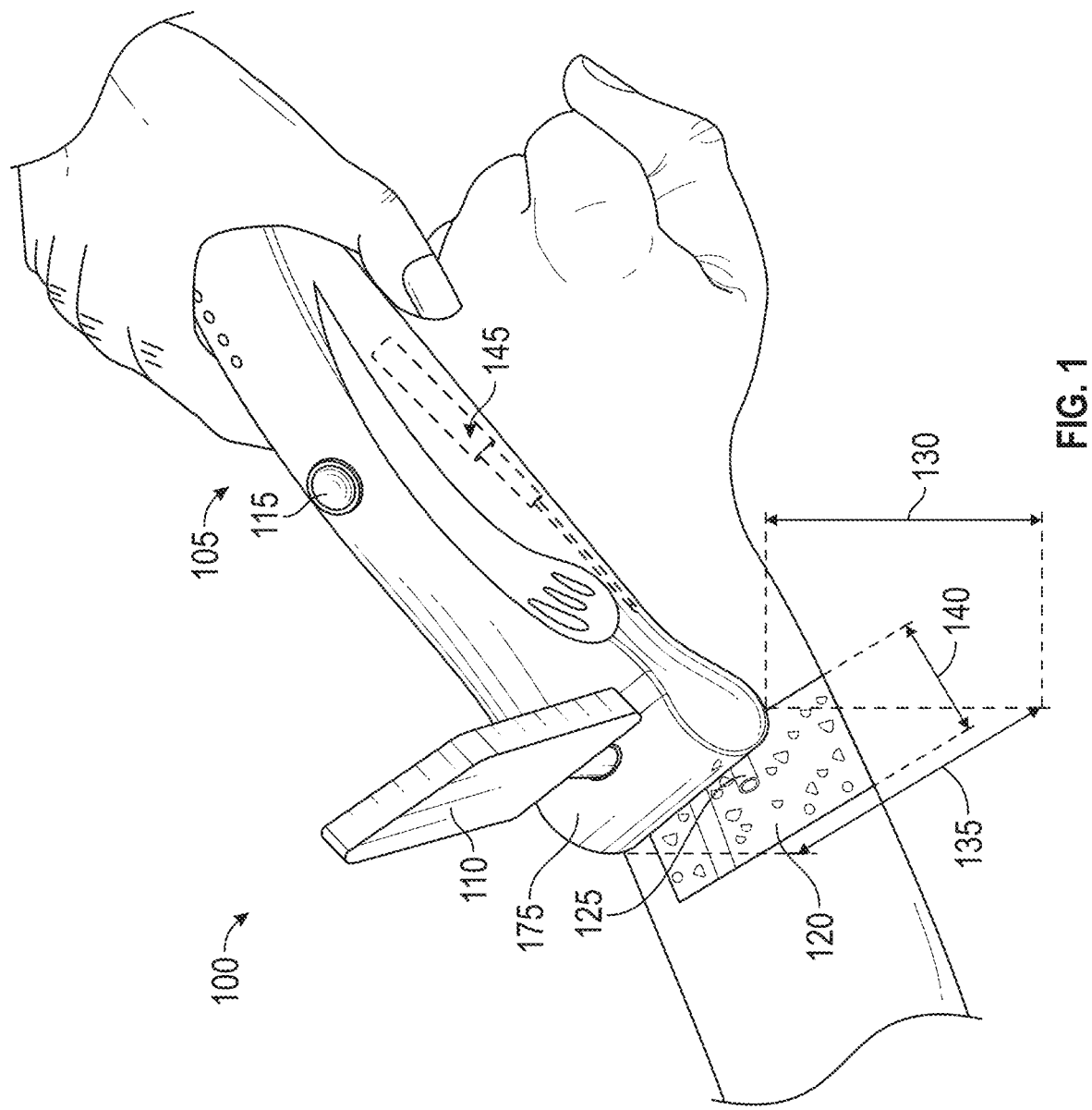
FIG. 1 is a perspective view of an intravenous therapy system according to some embodiments of the present disclosure.

In the present specification and in the appended claims the term "proximal" refers to a location on the needle of an intravenous therapy system that, during use, is closest to the clinician using the intravenous therapy system and farthest from the patient in connection with whom the device is used. Conversely, in the present specification and in the appended claims the term "distal" refers to a location on the needle of an intravenous therapy system that, during use, is farthest from the clinician using the intravenous therapy system and closest to the patient in connection with whom the intravenous therapy system is used.

In the present specification and in the appended claims the terms "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the device and toward the patient's skin.

In the present specification and in the appended claims the term "in" or "inwardly" refers to a location with respect to the needle of this intravenous therapy system that, during use, is toward the inside of the intravenous therapy system. Conversely, in the present specification and in the appended claims the term "out" or "outwardly" refers to a location with respect to the needle of this intravenous therapy system that, during use, is toward the outside of the intravenous therapy system.

In the present specification and in the appended claims the term "vascular access device" (VAD) may refer to any tubing inserted into a blood vessel (e.g., vein or artery) used to administer fluids into a patient's bloodstream, monitor pressures, or collect a blood sample from the patient. VADs may include a peripheral intravenous device and a central venous access device among others. During operation of the handheld ultrasound probe of the intravenous therapy systems described herein, the VAD recommendation module may be executed to describe on the display device of the handheld ultrasound probe which VAD to use based on a vascular anatomy of the patient.

In the present specification and in the appended claims, the term "coronal plane" or coronal view" refers to a plane or view of an interior of a patient's body resulting from a division of a patient's body into anterior and posterior portions. In a specific example, a coronal plane of a patient's arm would be a plane that runs through the long axis of the patients arm from the shoulder to the tips of the patient's fingers when the patient's arm is oriented to the side of the patient with the patient's palm facing anterior.

In the present specification and in the appended claims, the term "transverse plane" or transverse view" refers to a plane or view of an interior of a patient's body resulting from a division of a patient's body into upper and lower portions. In a specific example, a transverse plane of a patient's arm would be a plane that runs through the short axis of the patients arm from an anterior side of the patient's arm to a posterior side of the patient's arm when the patient's arm is oriented to the side of the patient with the patient's palm facing anterior.

This invention is described herein using like reference numbers for like elements in the different embodiments. Although the embodiments described herein are used in connection for use as an intravenous therapy system to receive a blood sample or introduce a medicament into the body of a patient, it is to be understood that this intravenous therapy system is applicable to other medical devices where it is desirable for a needle to be inserted into a blood vessel of a patient. In addition, while the embodiments of the intravenous therapy system are satisfied by embodiments in many different forms, there are shown in the drawings and herein described in detail, preferred embodiments of the invention with the scope of the disclosure measured by the appended claims.

FIG. 1 is a perspective view of an intravenous therapy system according to some embodiments of the present disclosure. In an embodiment, the intravenous therapy system 100 described herein includes a housing 105, part of which, used to be held by a clinician or other healthcare provider during operation of the intravenous therapy system 100. The housing 105 may be formed out of any material that may house other components of the intravenous therapy system 100 as described herein.

The intravenous therapy system 100 may include an ultrasound (US) probe 175 formed, in an embodiment, at a distal end of the housing 105 of the intravenous therapy system 100. The US probe 175 may be handheld. The US probe 175 may be any device that converts electrical signals from an electrical source into ultrasound waves and converts ultrasound waves received at the US probe 175 into electrical signals. During operation of the US probe 175, the US probe 175 may receive an electrical signal and convert that electrical signal into ultrasound waves that are directed, either continuously or pulsed, to enter into a part of a patient's body. As the ultrasound waves enter the patient's body, those ultrasound waves may be reflected off of structures within the patient's body and reflected back to the US probe 175. When the reflected ultrasound waves reach the US probe 175 within a window of time, sometimes corresponding to a time it takes for the energy to pass through a depth of the patient's body, the US probe 175 converts those ultrasound waves back into electrical signals. These electrical signals may be interpreted by a processor housed within the housing 105 of the intravenous therapy system 100 and used to form an image of the internal structures within the patient's body. In an embodiment presented herein, the electrical signals presented to the processor and used to form the images of the structures within the patient's body may be displayed at a video display device of the intravenous therapy system 100. In a specific application and during operation of the intravenous therapy system 100, the US probe 175 may be directed towards and in contact with, an arm of the patient in order to detect a position of a blood vessel 125 within the patient's arm.

As described herein, intravenous therapy system 100 also includes a video display device 110 communicatively coupled to the US probe 175 and the processor within the housing 105 among other components of the intravenous therapy system 100. In an embodiment, the video display device 110 may receive input from the processor descriptive of the data received by the US probe 175. This input from the processor causes images of the structures within the patient's body to be presented on the video display device 110. The images presented may change as the position of the US probe 175 placed against the patient's body changes. In some embodiments, the US probe 175 may include one or more US sensors, which may provide a transverse view of the blood vessel 125, a coronal or longitudinal view of a blood vessel 125, or another view based on a position of the US probe 175. In some embodiments, the US sensors may be arranged in a two-dimensional array.

In an embodiment, the data from the US probe 175 sent to the processor may be data descriptive of the transverse view of the structures of the blood vessel 125 such as a vein within a patient's arm that are on a transverse plane 120 of the arm. In any embodiment presented herein, however, it is understood that the US probe 175 may be placed against any portion of the patient's body such as a leg in order to locate and access a blood vessel 125 with a VAD.

In an embodiment, the data from the US probe 175 sent to the processor may be data descriptive of a coronal view of the structures such as a vein within a patient's arm that are on a coronal plane 140 of the arm. The view along the coronal plane 140 may be the longitudinal view of a blood vessel of the patient that runs the length of the patient's arm. The video display device 110 may display either or both of the coronal planar view along the coronal plane 140 of the patient, the transverse planar view along the transverse plane 120 of the patient, or both.

In the embodiments presented herein, the housing 105 may also house the magnetic field detector (not shown), which may include one or more magnetic field sensors that are used to detect the presence of a metal. In specific embodiments presented herein, the magnetic field detector may detect any metal components of a VAD to be inserted into the patient. In an embodiment, the magnetic field detector may detect the location of the metal components of the VAD relative to the US probe 175. In these embodiments, the processor of the intravenous therapy system 100 may overlay positional location data related to the location and the projected position of the needle tip of the VAD onto any images presented on the video display device 110, such as the cross section of the vein. By way of example, when the video display device 110 displays a coronal plane 140 of the patient's arm, the video display device 110 may show the movement of the VAD passing into the blood vessel 125. Similarly, when the video display device 110 display a transverse plane 120 of the patient's arm, the video display device 110 may show a trajectory point to which the VAD is going to intersect with the blood vessel 125.

In an embodiment, the intravenous therapy system 100 is a stand-alone system that may communicate, wirelessly with other networked computing systems. In order to operate, the housing 105 of the intravenous therapy system 100 may include a battery (not shown). The battery may include, in some embodiments, a smart battery system or be operatively coupled to a power management unit that tracks and provides power state data. This power state data may be stored with the instructions, parameters, and profiles to be used with the systems and methods disclosed herein.

In the embodiments presented herein, the intravenous therapy system 100 may be communicatively coupled to a processor (not shown). In an embodiment, the intravenous therapy system 100 may be a stand-alone device that includes, within the housing 105, the processor. In another embodiment, the intravenous therapy system 100 may be communicatively coupled to a processor exterior or remote to the housing 105 of the US probe 175. In the embodiments presented herein, the processor may include the hardware architecture used to retrieve computer readable program code from a data storage device also housed within the housing 105 and execute that computer readable program code. In an embodiment, the computer readable program code executed by the processor causes the intravenous therapy system 100 to perform the functions as described herein. In specific embodiments, the execution of the computer readable program code may cause the US probe 175 to receive electrical signals, convert those electrical signals into ultrasonic waves, cause those waves to be propagated into a patient's body, receive reflected ultrasonic waves, and provide data to the processor indicative of the structures present within the patient's body. In an embodiment, the execution of the computer readable program code may cause a magnetic field detector to detect the presence and location of a portion of a VAD. The processor may also execute computer readable program code that causes the location data descriptive of the location and/or the projected path of the VAD to be overlaid onto ultrasonic images presented by the processor during operation of the US probe 175. As such, the execution of the computer readable program code causes the intravenous therapy system 100 to operate such that a clinician or other HCP may accurately and precisely access a patient's blood vessel with little to no inaccurate placements of that VAD. Additionally, according to an embodiment of the present specification, the execution of the computer readable program code may allow the clinician or other HCP to assess the placement and indwelling of the VAD after the clinician or other HCP has successfully inserted the VAD into the patient's blood vessel.

In some embodiments presented herein, the housing 105 may include a VAD chassis 145. The VAD chassis 145 may be formed into a portion of the housing 105 that is closest to the patient's body. During operation of the intravenous therapy system 100, a VAD within the VAD chassis 145 may be automatically advanced in order to allow for the automatic insertion of the VAD into the patient's body. In the embodiments presented herein, the VAD chassis 145 may be communicatively coupled to the processor so as to receive data descriptive of a trajectory of the VAD placed within the VAD chassis 145. The data is descriptive of the direction the VAD is to take in order to cause the VAD to intersect with a blood vessel within the patient's body. In these embodiments, the US probe 175 and magnetic field detectors may provide data on a closed-loop feedback in order to direct the VAD into the patient's blood vessel as the VAD engages the patient's skin and the VAD is directed through the patient's body.

In the embodiments herein, the VAD chassis 145 may include a VAD advancement system that includes a motor, which may include a linear motor, a rotational motor, or any other suitable type of motor. The VAD advancement system may receive signals from the processor as described herein in order to advance the VAD into the patient's body using the motor. In some embodiments presented herein, the motor may be a linear motor that produces a linear force along its length. This may allow the motor to pass the VAD loaded into the VAD chassis 145 away from the housing 105 of the intravenous therapy system 100 and into the body of the patient. In an embodiment, the motor may also allow for the tilt movement, the rotation movement, and the yaw movement of the VAD during insertion. The linear, tilt, rotational, and yaw adjustments of the direction of the VAD allows for the VAD to intersect with the blood vessel of the patient in situations where the intravenous therapy system 100 is moved, either deliberately or accidentally, along the surface of the patient's body.

In an embodiment, the intravenous therapy system 100 may include an audio feedback device, a haptic feedback device, visual feedback, or a combination thereof, in order to indicate when the VAD being inserted into the blood vessel within the patient's body is determined to be on an intersecting trajectory into a blood vessel of the patient. In an embodiment, the intravenous therapy system 100 may include another audio feedback device, another haptic feedback device, another visual feedback, or a combination thereof, in order to indicate if the VAD being inserted into the blood vessel within the patient's body is determined to not be on an intersecting trajectory into a blood vessel of the patient.

In some embodiments, the audio feedback device, a haptic feedback device, visual feedback, or a combination thereof may indicate to a clinician or other HCP when the VAD is aligned to intersect or misaligned so as to not be able to intersect with the patient's blood vessel and may indicate how to properly orient the intravenous therapy system 100 so as to allow for that intersection to occur. By way of example, the video display device 110 may visually indicate that the VAD is not on a trajectory to intersect with the patient's blood vessel and may provide visual indications as to how to orient the intravenous therapy system 100 on the patient's body using x-, y-, and z-coordinate information. An audio signal produced by a speaker of the intravenous therapy system 100 may audibly provide feedback indicative of such a misalignment. Additionally, once proper alignment is established, a haptic feedback device such as a tumbler may be used to indicate when the VAD is no longer on a trajectory that will cause the VAD to intersect with the patient's blood vessel based on movement of the haptic feedback device, the US probe 175, or the patient.

In some embodiments presented herein, the intravenous therapy system 100 may include a VAD recommendation module (not shown). In these embodiments, the VAD recommendation module may provide an audible or visual indicator that provides a suggestion as to which type of VAD to use in order to access the patient's blood vessel. An audible VAD recommendation may be presented via a speaker housed within the housing 105 of the intravenous therapy system 100. A visual VAD recommendation may be provided to the clinician or other HCP via the video display device 110. In any of these examples, the clinician or other HCP may be allowed to provide data descriptive of the purpose of the VAD prior to the VAD recommendation module providing the recommendation. Such data may indicate whether the purpose of the VAD is to retrieve a blood sample or whether the purpose of the VAD is to provide an infusing fluid such as a saline solution, a medicament, and/or a parenteral nutrition into the patient's bloodstream. The length of time the VAD is to remain in the patient's blood vessel may also be input by the clinician or other HCP in order for the VAD recommendation module to provide a more accurate VAD recommendation.

In an embodiment, the VAD recommendation module may be computer readable program code stored on a memory device, data storage device, or other device used to store computer readable program code. The computer readable program code, in an embodiment may be accessed by the processor in order to execute that computer readable program code. The execution of that computer readable program code may bring about the assessment of and presentation to the clinician or other HCP of the VAD recommendation. In another embodiment, the VAD recommendation module may be an application specific integrated circuit (ASIC). In this embodiment, the processor may access the ASIC in order to bring about the assessment of and presentation to the clinician or other HCP of the VAD recommendation.

The intravenous therapy system 100 may include any computer readable program code used to be executed by the processor in order to initiate the functionalities described herein. During execution of the computer readable program code, any number of signals may be presented by the processor to any of the US probe 175, magnetic field detector, VAD advancement system, motor, audio feedback device, haptic feedback device, visual feedback, or video display device 110 so as to initiate the functionalities of these devices as described herein. In an alternative embodiment, any number of ASICs may be used to replace or augment the computer readable program code in order to initiate the functionalities of these devices as described herein.

The intravenous therapy system 100 may further include one or more VAD buttons 115, which may include one or more advancement buttons configured to advance the needle and the catheter in the distal direction, one or more retraction buttons configured to withdraw the needle in the proximal direction, one or more pivot or angle adjustment buttons configured to change a position of the VAD. In some embodiments, the VAD may be advanced distally when a particular button 115 is pressed. In some embodiments, the VAD may be advanced distally when the particular button 115 is pressed and the needle is projected to be positioned within the targeted vein.

The VAD button 115 may be communicatively coupled to the VAD advancement system and the motor so that actuation of the VAD button 115 causes the VAD to advance into the patient's arm when pressed, or when pressed and aligned such that the needle is projected to properly intersect with the targeted vein. The actuation of the VAD button 115 by the clinician or other HCP may start the advancement of the VAD based on the data received by the US probe 175 and the magnetic field detector, which may include magnetic field sensors.

The data received by the US probe 175 and magnetic field detector may indicate that the VAD is on a trajectory to intersect with a blood vessel within the patient's body and detected by the US probe 175. The advancement of the VAD may continue so long as the data, on a continuous feedback loop, from the US probe 175 and magnetic field detector indicates that the VAD is on that trajectory to intersect with the blood vessel. In an embodiment, if and when the data from the US probe 175 and magnetic field detector indicates that the VAD is no longer on an intersecting trajectory with a blood vessel, the actuation of the VAD button 115 by the clinician or other HCP may be overridden and stop the advancement and the audio feedback device, a haptic feedback device, visual feedback, or a combination thereof may so indicate to the clinician or other HCP. The clinician or other HCP may then orient the intravenous therapy system 100 so the needle is back on target to intersect the vein, and the actuation of the VAD button 115 may once again be recognized and the placement of the VAD may continue.

Figure 2:
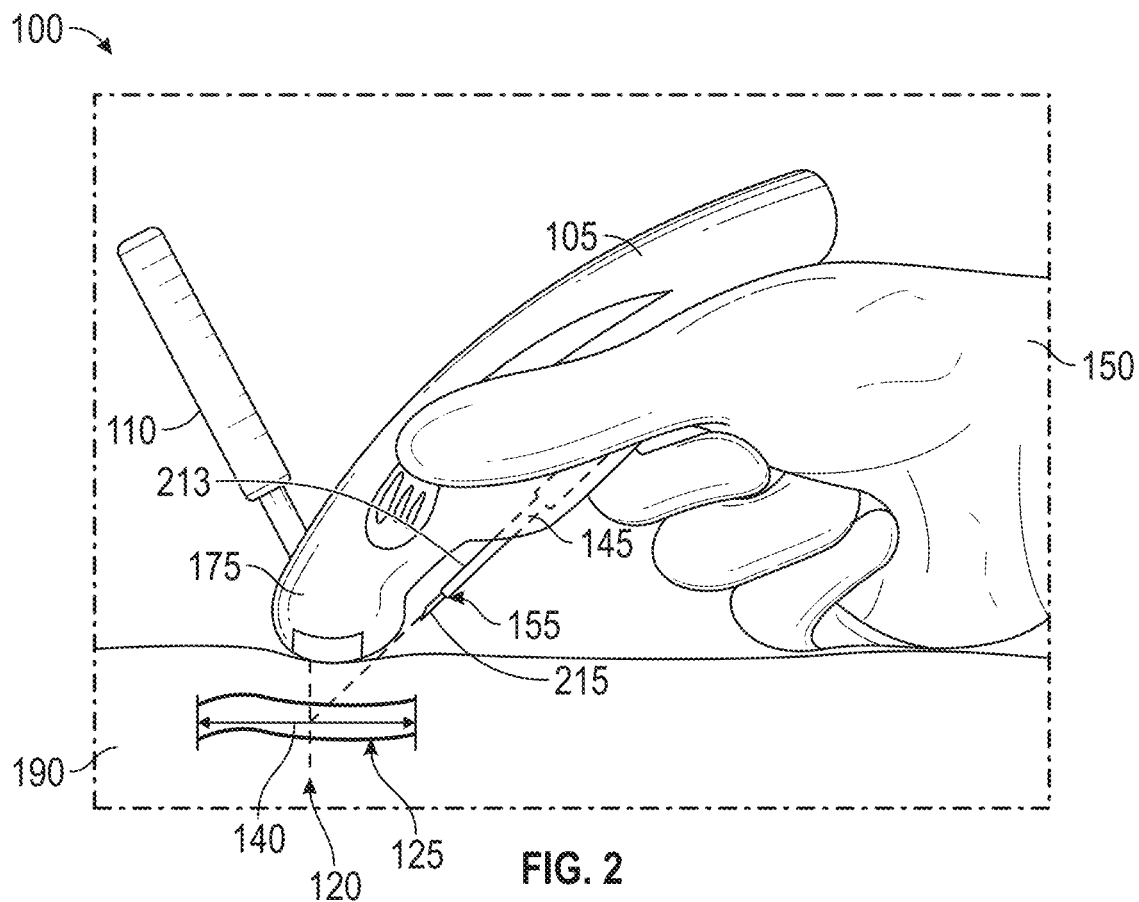
FIG. 2 is a side view of an intravenous therapy system interfacing with a patient's arm according to some embodiments of the present disclosure.

FIG. 2 is a side view of an intravenous therapy system 100 interfacing with a patient's arm 190 according to some embodiments of the present disclosure. The intravenous therapy system 100 shows that the US probe 175 is interfacing with the patient's arm 190. In the embodiment shown in FIG. 2, the intravenous therapy system 100 is being held by the hand 150 of the clinician or other HCP. In the embodiment shown, the clinician or other HCP uses a single hand 150 to hold the intravenous therapy system 100. In some embodiments, the VAD chassis 145 may not be included and instead the clinician or other HCP, after receiving a VAD recommendation from the VAD recommendation module, use a second hand to place and insert the VAD at and into the patient's arm 190. With the inclusion of the video display device 110 on the housing 105 of the intravenous therapy system 100, the clinician or other HCP may situate the intravenous therapy system 100 and handheld VAD while using the video display device 110 to orient the VAD sufficiently and, based on the data presented on the video display device 110, direct the VAD into the patient's blood vessel.

In the embodiment where the VAD chassis 145 is present on the housing 105 of the intravenous therapy system 100, a processor may direct the VAD advancement system of the VAD chassis 145 to engage the motor. The motor may, based on the data received by the US probe 175 and magnetic field detector, move the VAD inserted into the VAD chassis 145 into the patient's arm 190 in order to cause the VAD to intersect with a blood vessel within the patient's arm.

During operation, the clinician or other HCP may orient the intravenous therapy system 100 onto a portion of the patient's body such as the patient's arm 190 into which the VAD is to be inserted. The US probe 175 may then detect the structures within the patient's arm 180. The data descriptive of the structures, such as a blood vessel 125, may be relayed to the video display device 110 to present a visual display of these structures to a clinician or other HCP. In an embodiment, the video display device 110 may present a view of the blood vessel 125 on a transverse plane 120. This view may present to the clinician or other HCP a "cross-sectional" view of the blood vessel 125 so that the clinician or other HCP may assess whether that blood vessel 125 or some other blood vessel 125 is to be accessed by the VAD. In an embodiment, the transverse plane 120 may have a length 135 and a width 130. In an embodiment, the video display device 110 may present a view of the blood vessel 125 on a coronal plane 140. This view may present to the clinician or other HCP a longitudinal view of the blood vessel 125 as the blood vessel 125 runs along the long axis of the patient's arm 190. In an embodiment, the video display device 110 may present or be capable of presenting both the transverse plane 120 and coronal plane 140 as detected by the US probe 175.

The intravenous therapy system 100 may also include a magnetic field detector (not shown) placed close to the US probe 175. The magnetic field detector may detect the presence and location of any parts of the VAD, which may be magnetically permeable. During operation, the magnetic field detector may receive data regarding the location of the parts of the VAD and cause an image descriptive of that location of the VAD to be overlaid onto either or both views of the transverse plane 120 and coronal plane 140. As such, the clinician or other HCP may view the movement of the VAD as it moves towards and into the patient's arm 190 so as to determine that the trajectory 155 of the VAD is appropriate to intersect with the blood vessel 125.

In the embodiment where the intravenous therapy system 100 does not include a VAD chassis 145 and VAD advancement system, the clinician or other HCP may hold the intravenous therapy system 100 with one hand 150 and, with the opposite hand, orient and move a VAD towards and into the patient's arm 190. By consistently viewing the video display device 110 housed on the housing 105 of the intravenous therapy system 100, the clinician or other HCP may more accurately view the trajectory 155 of the VAD as the clinician or other HCP attempts to access the blood vessel 125. Thus, the clinician or other HCP may be provided with real-time data descriptive of the VAD relative to the blood vessel 125 using the data presented on the video display device 110 from the US probe 175 and magnetic field detector. This allows the clinician or other HCP to more accurately and precisely access the blood vessel 125 with little to no additional trauma to the patient's body. This increases the efficiency of VAD placements by the clinician or other HCP resulting in better healthcare to the patient.

The present specification describes the access of a blood vessel 125 by the VAD generally. However, it is contemplated by the present disclosure that any specific type of blood vessel 125 may be accessed for specific medical purposes. For example, the blood vessel 125 described herein may be a vein into which a saline solution, a medicament, and/or a parenteral nutrition is to be presented into the patient's bloodstream. In this case, the vein may pass the saline solution, a medicament, and/or a parenteral nutrition to the heart of the patient which then distributes the saline solution, a medicament, and/or a parenteral nutrition into the remaining portions of the patient's body. Still further, the blood vessel 125 may be an artery into which, for other medical reasons, the saline solution, a medicament, and/or a parenteral nutrition may be introduced. In either embodiment, the US probe 175 may detect the movement of blood within the blood vessel 125 and determine whether the blood vessel 125 is a vein or artery.

In an embodiment, a clinician or other HCP may input to the intravenous therapy system 100 an indication that a vein is to be accessed. In this embodiment, the US probe 175 may provide data descriptive of a vein to be accessed. In an embodiment, the processor may cause the vein to be visually highlighted on the video display device 110 by, for example, drawing a line or other indicator around a transverse plane 120 view of the vein. In an embodiment, the video display device 110 may be a touchscreen video display device 110 that allows a user to determine which blood vessel 125 is to be accessed by inputting on the screen of the video display device 110 a line or other indicator descriptive of a target blood vessel 125. In either embodiment, the processor of the intravenous therapy system 100 may use the line or other indicator descriptive of a target blood vessel 125 to direct the insertion of the VAD by either appropriately actuating the motor of the VAD advancement system or directing the clinician or other HCP on how to adjust the trajectory 155 of the VAD during insertion.

In an embodiment, the housing 105 of the intravenous therapy system 100 may include a battery (not shown). The battery may include, in some embodiments, a smart battery system or be operatively coupled to a power management unit that tracks and provides power state data. This power state data may be stored with the instructions, parameters, and profiles to be used with the systems and methods disclosed herein.

In an embodiment, the intravenous therapy system 100 may include a network interface device that communicatively couple the intravenous therapy system 100 to a computer network. In these embodiments, the intravenous therapy system 100 may be communicatively coupled to an electronic health record (EHR) database. The EHR database may be a database that maintains patient-specific health care records. In an embodiment, the intravenous therapy system 100 may relay the use of a VAD on the patient as well as a record (either video or still images) of the placement of the VAD and the ultrasound data received at the US probe 175. This record may be maintained in order to create a relatively more robust health care record for a given patient.

In any embodiment described herein, the intravenous therapy system 100 may be communicatively coupled to the EHR system or other computing device via a data and power cable. In this embodiment, the data and power cable may be used when the intravenous therapy system 100 does not include a network interface and/or when the intravenous therapy system 100 does not include its own power source such as the battery described herein. In either example, the communication to the EHR system may allow for further communication to other computing devices of a network of computing devices.

Figure 3:
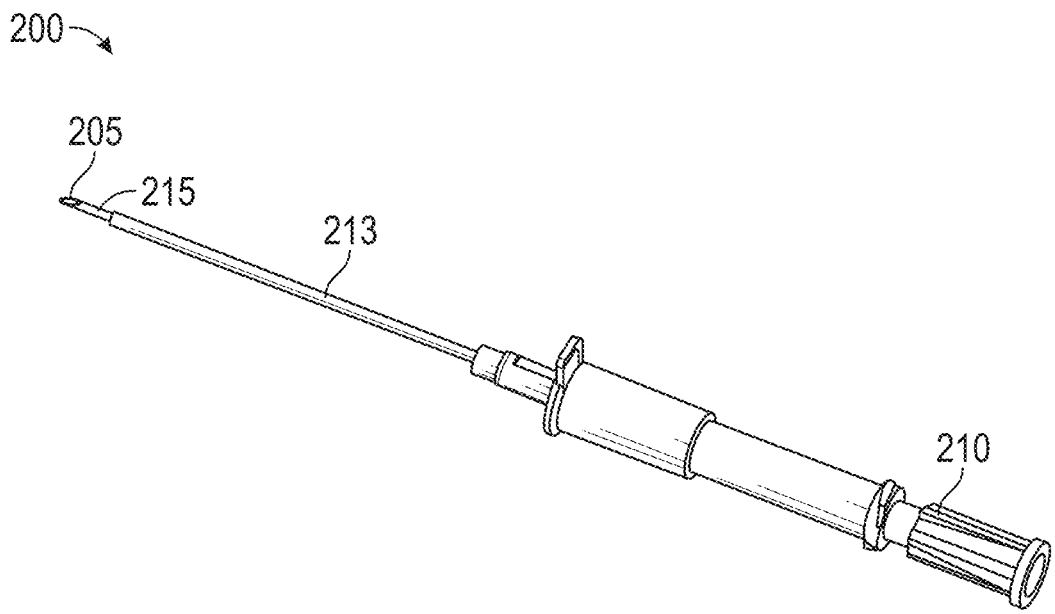
FIG. 3 is side view of a VAD according to some embodiments of the present disclosure.

FIG. 3 is side view of a VAD 200 according to some embodiments of the present disclosure. The VAD 200 may be any device that is formed to access a patient's blood vessel in order to access a blood sample or deliver a saline solution, a medicament, and/or a parenteral nutrition into the patient's bloodstream.

The example VAD 200 presented in FIG. 3 includes a distal end 205 and a proximate end 210. In this example, the VAD 200 may include a needle 215 that is made of a metallic material that is capable of being magnetized. The VAD 200 may include a catheter 213, which may include a peripheral intravenous catheter, a midline catheter, or a peripherally inserted central catheter. The needle 215 may be hollow so as to be able to pass a blood sample, saline solution, a medicament, and/or a parenteral nutrition therethrough. At the distal end 205, the needle 215 may be beveled to create a point or sharp so as to more easily pass through the skin and body tissues of the patient's body while accessing the blood vessel as described herein.

The VAD 200 ma include any other elements that may fit a particular function during the blood sampling or blood infusion processes. By way of example, the VAD 200 may include a plastic coupling device used to couple the VAD 200 to a reservoir of saline solution, a medicament, and/or a parenteral nutrition or to a blood sampling vile. Because the intravenous therapy system may implement the use of any type of VAD 200, the specific details of the VAD 200 may vary from use to use. However, the present specification contemplates the use of any VAD 200 that is configured for insertion into the body of the patient.

Figure 4:
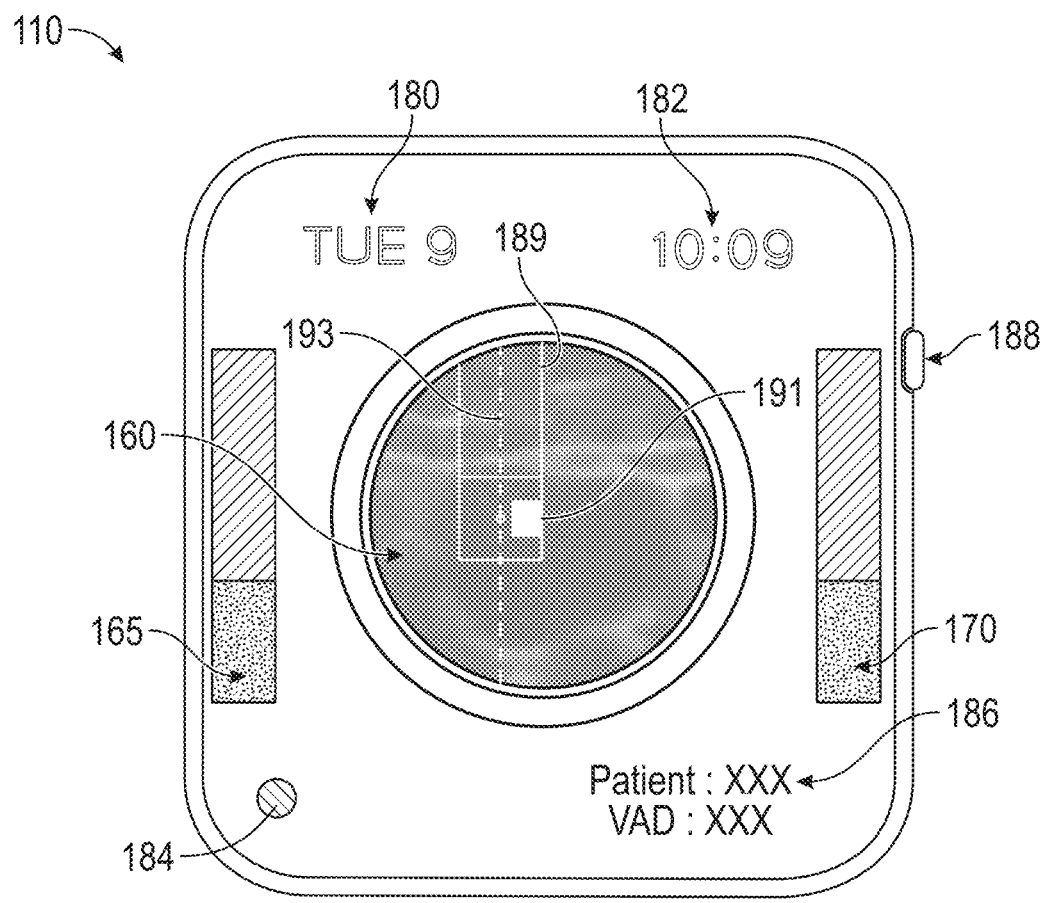
FIG. 4 is a graphical view of a video display device according to some embodiments of the present disclosure.

FIG. 4 is a graphical view of a video display device 110 according to some embodiments of the present disclosure. As described herein, the video display device 110 receives data descriptive of the structures internal to a patient's body and, specifically, a blood vessel. The data is received by the processor from the US probe 175 and magnetic field detector and used to form the transverse plane 120 and coronal plane 140 images of the structures within the patient's body as well as calculate projection of the trajectory of the needle, such as, for example, the needle 215, based on the position of the needle tip relative to the US probe 175 and known geometries of the particular VAD (gauge, length, catheter brand, etc.) being used.

The image presented in FIG. 4 is a transverse plane 120 image 160 of a blood vessel within the patient. However, the present specification contemplates that multiple different views including one along a coronal plane 140 of the blood vessel may be alternatively or additionally displayed at the video display device 110. In a specific embodiment, the video display device 110 may include a number of input buttons 188. In this embodiment, actuation of the input buttons 188 may switch the view presented to the user. A dimensional reference indicator may also be included on the video display device 110 to allow a clinician to measure or have a reference for estimating a size of the patient's anatomy (such as vein diameter or vein depth).

FIG. 4 illustrates a projected path 189 of the needle, according to some embodiments. FIG. 4 also illustrates a projected position 191 of where the needle tip will intersect a plane of the image 160 based on a trajectory 193 or path of movement of the needle. In response to the projected position 191 being centered or properly aligned with respect to the blood vessel 125, conditions may be appropriate for advancement of the VAD (manually by the clinician or automatically as discussed herein).

The video display device 110 may present to the user any data in additional to the transverse plane 120 and coronal plane 140 images 160. By way of example, the video display device 110 may include the current date 180 and time 182 the intravenous therapy system is being used. The date 180 and time 182 may be used during the recording of the ultrasound and VAD insertion at the EHS described herein. This may be used to accurately date and document the procedure conducted by the clinician or other HCP.

Additionally, the video display device 110 may display a current ultrasound resolution 184 being viewed on the image 160. In an embodiment, the input buttons 188 may be used to adjust the resolution of the image 160 so that a clinician or other HCP may see further detail of a blood vessel being presented.

Still further, the video display device 110 may display patient and VAD information 186. The patient information may include the name of the patient, an assigned number related to the patient and the patient's EHR, as well as medically relevant medical data related to the patient such as blood vessel geometry, a date of birth, weight, current blood pressure, current pulse, among other data. The VAD information may include data descriptive of the type of VAD being used by the clinician or other HCP, the name or identity of the clinician or HCP, and recommended to be used by the VAD recommendation module, among other data.

The video display device 110 may further include a number of VAD trajectory indicators 165 and 170. In an embodiment, a first VAD trajectory indicator 165 may be used to indicate a depth within the patient's body the VAD is at. The first VAD trajectory indicator 165 may be color coded to indicate whether the depth of the VAD as it passes through the patient's body is in line with a processor-calculated trajectory. If the VAD is not at the correct depth at any given time during insertion of the VAD, the first VAD trajectory indicator 165 may visually indicate an improper trajectory by, for example, changing colors. The visual indication of a wrong trajectory may be accompanied with, in some examples, an audible warning from a speaker, a haptic feedback warning from a haptic device within the intravenous therapy system, or a combination of any of these three warning devices. As such, during use, a clinician or other HCP may accurately adjust the trajectory of the VAD, or intravenous therapy system based on the trajectory the VAD is to follow in order to intersect with a detected blood vessel.

In an embodiment, a second VAD trajectory indicator 170 may be used to indicate x- and y-coordinates within the patient's body the VAD is at. The second VAD trajectory indicator 170 may be color coded to indicate whether the placement of the VAD as it passes through the patient's body is in line with a processor-calculated trajectory. The second VAD trajectory indicator 170 may indicate how far along the projected path 189 the needle tip is and a distance of the needle tip from the targeted vein. If the VAD is not at the correct x- and y-coordinate at any given time during insertion of the VAD, the second VAD trajectory indicator 170 may visually indicate an improper trajectory by, for example, changing colors. The visual indication of a wrong trajectory may be accompanied with, in some examples, an audible warning from a speaker, a haptic feedback warning from a haptic device within the intravenous therapy system, or a combination of any of these three warning devices. As such, during use, a clinician or other HCP may accurately adjust the trajectory of the VAD, or intravenous therapy system based on the trajectory the VAD is to follow in order to intersect with a detected blood vessel.

As described herein, the video display device 110 may include a touchscreen layer. The touchscreen layer may allow a clinician or other HCP to provide input to the intravenous therapy system. An example of this input may include blood vessel indication data. In this specific example, the clinician or other HCP, upon seeing a blood vessel such as a vein presented on the image 160 of the internal structures of the patient's body, may circle or otherwise indicate where the VAD is to intersect with the blood vessel. This indication, along with the data received by the processor of the intravenous therapy system from the US probe and magnetic field detector, may be used to calculate the trajectory of the VAD by the processor. Once the trajectory is calculated, the trajectory may be used during automatic insertion of the VAD by a VAD advancement system or manual insertion of the VAD by a clinician or other HCP. The present specification further contemplates that the intravenous therapy system may be moved by the clinician or other HCP during insertion of the VAD. In this embodiment, the video display device 110 may also include any other indicator on the screen that may indicate to the clinician or other HCP to keep the target blood vessel on the screen by readjusting the intravenous therapy system relative to the patient's body.

Figure 5A:
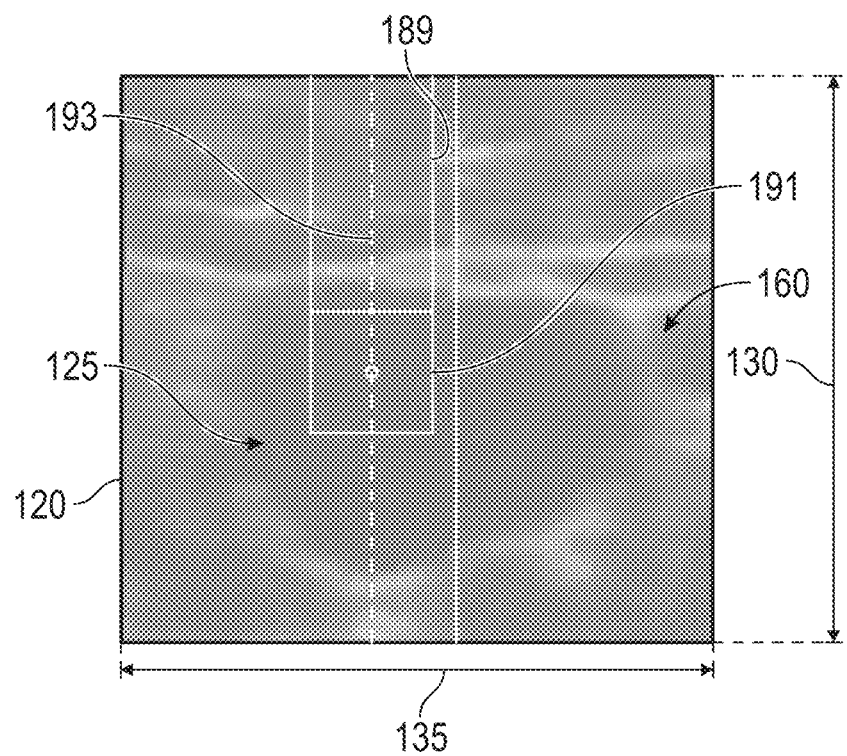
FIG. 5A is a graphical view of a blood vessel along a transverse plane according to an embodiment of the present disclosure.

FIG. 5A is a graphical view of a blood vessel 125 along a transverse plane 120 according to an embodiment of the present disclosure. The embodiment shown in FIG. 5A indicates a length 135 and width 130 that the image encompasses. The length 135 and width 130 may vary depending on a selected resolution as well as the ultrasonic capabilities of the US probe described herein.

The blood vessel 125 may be presented on the view of FIG. 5A by processing the data received by the US probe 175 by the processor. This view may change based upon movement of the intravenous therapy system relative to the patient's body. However, during operation the video display device 110 may indicate to a clinician or other HCP to hold the intravenous therapy system steady while engaged in the functionalities of the intravenous therapy system as described herein.

The view presented in FIG. 5A may also include a projected path 189 of the needle, according to some embodiments. FIG. 5A also illustrates a projected position 191 of where the needle tip will intersect a plane of the image 160 based on a trajectory 193 or path of movement of the needle. In response to the projected position 191 being centered or properly aligned with respect to the blood vessel 125, conditions may be appropriate for advancement of the VAD (manually by the clinician or automatically as discussed herein).

In some embodiments, a target area may be determined by processing the image 130 and determining a location of the blood vessel 125 based on the image 130. An angle and position of the needle may then be adjusted until the projected position 191 is within the target area. In response to the projected position 191 being centered or properly aligned with respect to the blood vessel 125, the VAD trajectory feedback may be provided, indicating the intravenous therapy system is on target and advancement of the VAD may proceed (manually by the clinician or automatically as discussed herein).

The projected position 191 may be processor-created or may be based on data received at the touchscreen of the video display device from the clinician or other HCP as described. During operation, one or more of the following may be used by the video display device to alter manual or automatic advancement of the VAD: the location data of the distal end of the VAD, the geometric data of the specific VAD, the projected position 191 of the needle and the US plane, the trajectory line 193, and the location of the targeted blood vessel 125. In some embodiments, the trajectory 155 created by the processor may take into consideration certain characteristics of the VAD such as whether the VAD includes a bent needle.

Figure 5B:
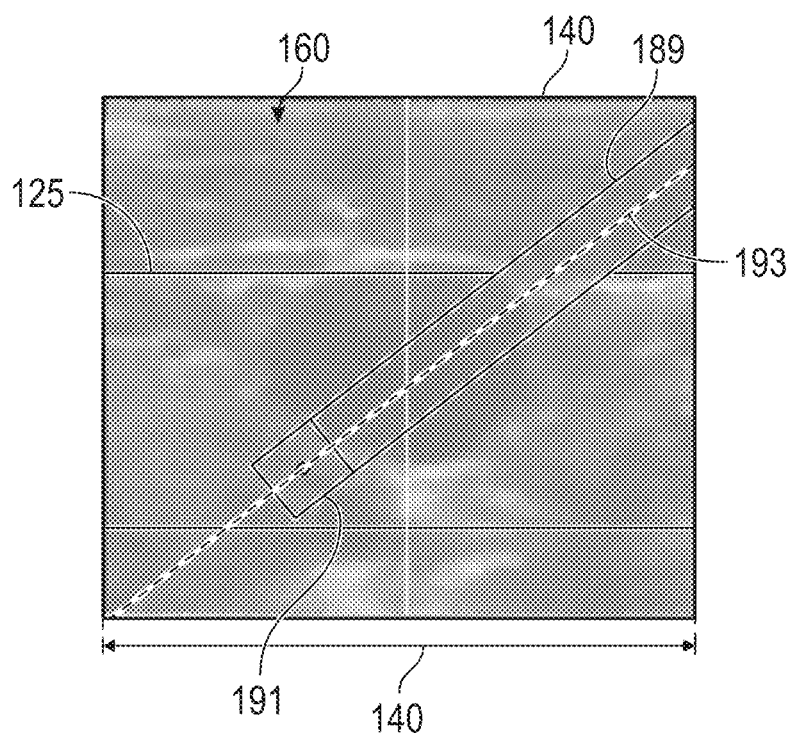
FIG. 5B is a graphical view of a blood vessel along a coronal plane according to an embodiment of the present disclosure.

FIG. 5B is a graphical view of a blood vessel 125 along a coronal plane 140 according to an embodiment of the present disclosure. In this view of the internal structures of the patient's body, the trajectory 155 may be at an angle relative to the blood vessel 125. Again, a target location 157 may be computed by the processor or indicated by the clinician or other HCP.

In the embodiment where the target location 157 is computed by the processor, the processor may use a number of types of data to create the target location 157. This data may include the detection of blood flow from the US probe 175, the differences in hues of colors presented on the view, the detection of movement of the exterior walls of the blood vessel, among other types of data. The present specification contemplates that any process may be executed to determine a proper placement of the VAD within the patient's blood vessel. In any embodiment, this data may be accumulated and updated to present to the clinician or other HCP on the display device where the VAD is to intersect with the blood vessel.

According to any embodiment presented herein, the coronal plane 140 and transverse plane 120 may not be the only planes at which the US probe 175 detects the internal structures of the patient's body. In some embodiments, the clinician or other HCP may manually select any variant of plane presented on the video display device 110 that may suit any particular need. Consequently, the present specification contemplates that other views may be presented apart from the transverse plane 120 and coronal plane 140 of FIGS. 5A and 5B, respectively, and those views on the video display device 110 are meant merely to be examples of data that may be presented to the clinician or other HCP. Further, in some embodiments, any view or plane of the patient's anatomy may be detected by adjustment or repositioning of the US probe 175.

Figure 6:
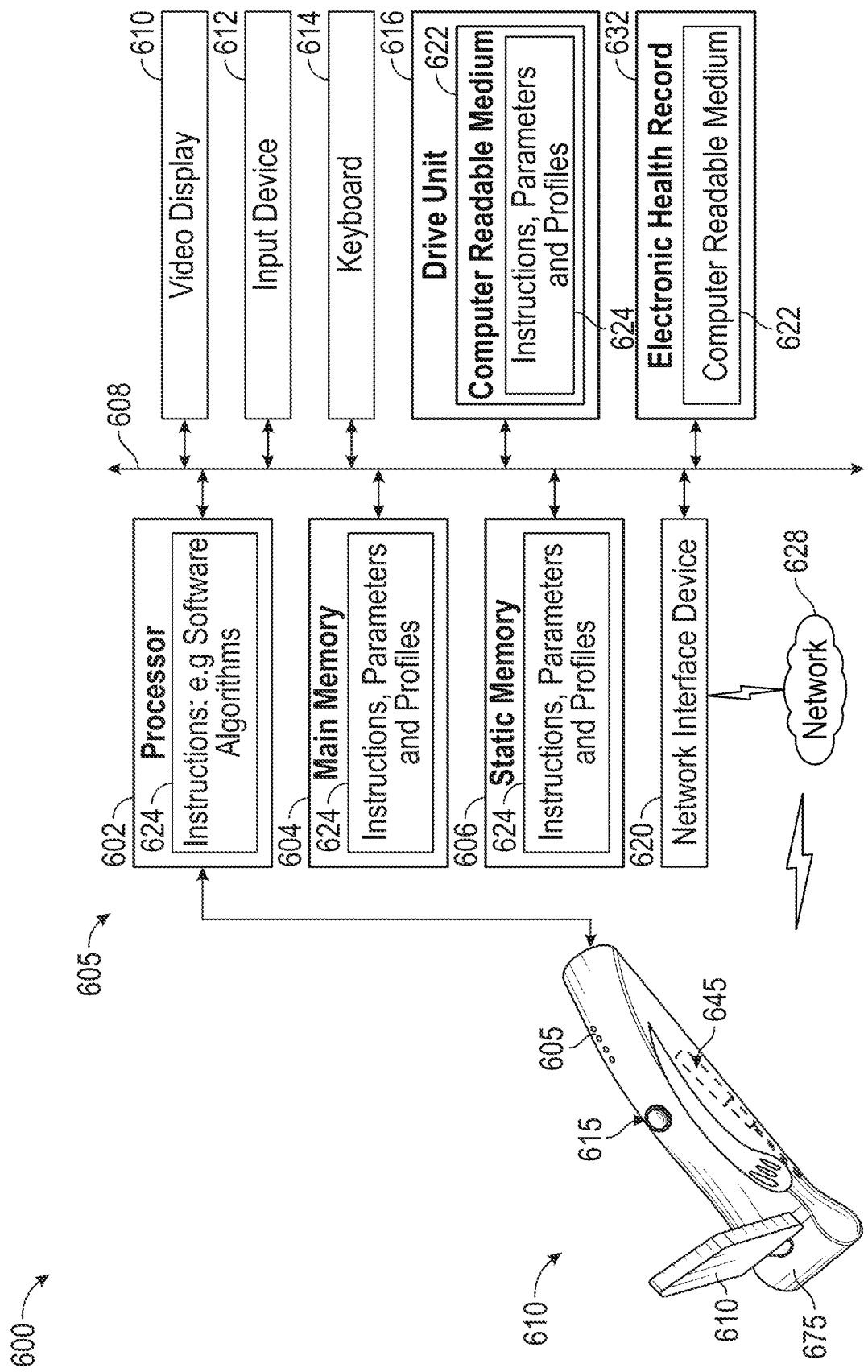
FIG. 6 is a block diagram of an intravenous therapy system according to an embodiment of the present disclosure.

FIG. 6 is a block diagram of an intravenous therapy system 600 according to an embodiment of the present disclosure. In the embodiments described herein, an intravenous therapy system 600 includes any instrumentality or aggregate of instrumentalities operable to compute, classify, process, transmit, receive, retrieve, originate, switch, store, display, manifest, detect, record, reproduce, handle, or use any form of information, intelligence, or data for business, scientific, control, entertainment, or other purposes. In the specific example shown in FIG. 6, the intravenous therapy system 600 includes a handheld blood vessel detection system 610 similar to the intravenous therapy system 100 shown in FIG. 1 and an information handling system 605. For example, an intravenous therapy system 600 can include as an information handling system 605 a personal computer, mobile device (e.g., personal digital assistant (PDA) or smart phone), server (e.g., blade server or rack server), a consumer electronic device, a network server or storage device, a network router, switch, or bridge, wireless router, or other network communication device, a network connected device (cellular telephone, tablet device, etc.), IoT computing device, wearable computing device, a set-top box (STB), a mobile information handling system, a palmtop computer, a laptop computer, a desktop computer, a communications device, an access point (AP), a base station transceiver, a wireless telephone, a land-line telephone, a control system, a camera, a scanner, a facsimile machine, a printer, a pager, a personal trusted device, a web appliance, or any other suitable machine capable of executing a set of instructions (sequential or otherwise) that specify actions to be taken by that machine, and can vary in size, shape, performance, price, and functionality.

In a networked deployment, the intravenous therapy system 600 may operate with a server or with a client computer in a server-client network environment, or as a peer computer system in a peer-to-peer (or distributed) network environment. In a particular embodiment, the intravenous therapy system 600 can be implemented using electronic devices that provide voice, video or data communication. For example, an intravenous therapy system 600 include any mobile or other computing device capable of executing a set of instructions (sequential or otherwise) that specify actions to be taken by that machine. Further, while a single intravenous therapy system 600 is illustrated, the term "system" shall also be taken to include any collection of systems or sub-systems that individually or jointly execute a set, or multiple sets, of instructions to perform one or more computer functions.

The blood vessel detection system 610 may be communicatively coupled to the information handling system 605 such as those computing devices described herein. In these embodiments, the information handling system 605 can include memory (volatile (e.g. random-access memory, etc.), nonvolatile (read-only memory, flash memory etc.) or any combination thereof), one or more processing resources, such as a central processing unit (CPU), a graphics processing unit (GPU), hardware or software control logic, or any combination thereof. Additional components of the information handling system 605 can include one or more storage devices, one or more communications ports for communicating with external devices, as well as, various input and output (I/O) devices, such as a keyboard, a mouse, a video/graphic display, or any combination thereof. The information handling system 605 can also include one or more buses operable to transmit communications between the various hardware components. Portions of an information handling system 605 may themselves be considered information handling systems 605.

Information handling system 605 can include devices or modules that embody one or more of the devices or execute instructions for the one or more systems and modules described herein, and operates to perform one or more of the methods described herein so as to interact with the blood vessel detection system 610. The information handling system 605 may execute code instructions 624 that may operate on servers or systems, remote data centers, or on-box in individual client information handling systems according to various embodiments herein. In some embodiments, it is understood any or all portions of code instructions 624 may operate on a plurality of information handling systems 605.

The information handling system 605 may include a processor 602 such as a central processing unit (CPU), control logic or some combination of the same. Any of the processing resources may operate to execute code that is either firmware or software code. In an embodiment, the processor 602 may interact with a processor of the blood vessel detection system 610 as descried herein. Moreover, the information handling system 605 can include memory such as main memory 604, static memory 606, computer readable medium 622 storing instructions 624 of the electronic health record (EHR) 632, and drive unit 616 (volatile (e.g. random-access memory, etc.), nonvolatile (read-only memory, flash memory etc.) or any combination thereof). The information handling system 605 can also include one or more buses 608 operable to transmit communications between the various hardware components such as any combination of various input and output (I/O) devices.

The information handling system 605 may further include a video display 611. The video display 611 in an embodiment may function as a liquid crystal display (LCD), an organic light emitting diode (OLED), a flat panel display, a solid-state display, or a cathode ray tube (CRT). In an embodiment, the video display 611 may present to a user those same views presented on the video display device 110 of the blood vessel detection system 610. Additionally, the information handling system 605 may include an input device 612, such as a cursor control device (e.g., mouse, touchpad, or gesture or touch screen input, and a keyboard 214.

The network interface device shown as wireless adapter 620 can provide connectivity to a network 628, e.g., a wide area network (WAN), a local area network (LAN), wireless local area network (WLAN), a wireless personal area network (WPAN), a wireless wide area network (WWAN), or other networks. Connectivity may be via wired or wireless connection. The wireless adapter 620 may operate in accordance with any wireless data communication standards. To communicate with a wireless local area network, standards including IEEE 802.11 WLAN standards, IEEE 802.15 WPAN standards, WWAN such as 3GPP or 3GPP2, or similar wireless standards may be used. In some aspects of the present disclosure, one wireless adapter 620 may operate two or more wireless links. In the embodiments described herein, the network interface device 620 may wirelessly couple the information handling system 605 with the EHR 632. In the embodiments described herein, the EHR 632 may receive data descriptive of a position of a needle within the body of a patient, a blood vessel within the body of the patient, and the information handling system 605 may relay that positional data to an indicator presented on the display device 110.

In some embodiments, software, firmware, dedicated hardware implementations such as application specific integrated circuits, programmable logic arrays and other hardware devices can be constructed to implement one or more of some systems and methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by firmware or software programs executable by a controller or a processor system. Further, in an exemplary, non-limited embodiment, implementations can include distributed processing, component/object distributed processing, and parallel processing. Alternatively, virtual computer system processing can be constructed to implement one or more of the methods or functionalities as described herein.

The present disclosure contemplates a computer-readable medium that includes instructions, parameters, and profiles 624 or receives and executes instructions, parameters, and profiles 624 responsive to a propagated signal, so that a device such as the blood vessel detection system 610 connected to a network 628 can communicate voice, video or data over the network 628. Further, the instructions 624 may be transmitted or received over the network 628 via the network interface device or wireless adapter 620.

The information handling system 605 can include a set of instructions 624 that can be executed to cause the computer system to perform any one or more of the methods or computer-based functions disclosed herein. Various software modules comprising application instructions 624 may be coordinated by an operating system (OS), and/or via an application programming interface (API). An example operating system may include Windows®, Android®, and other OS types. Example APIs may include Win 32, Core Java API, or Android APIs.

The disk drive unit 616 may include a computer-readable medium 622 in which one or more sets of instructions 624 such as software can be embedded. Similarly, main memory 604 and static memory 606 may also contain a computer-readable medium for storage of one or more sets of instructions, parameters, or profiles 624. The disk drive unit 616 and static memory 606 may also contain space for data storage. Further, the instructions 624 may embody one or more of the methods or logic as described herein. For example, instructions relating to the formation of a view of the internal structures within the patient's body by the processor may be part of those instructions 624. In a particular embodiment, the instructions, parameters, and profiles 624 may reside completely, or at least partially, within the main memory 604, the static memory 606, and/or within the disk drive 616 during execution by the processor 602 of information handling system 605. The main memory 604 and the processor 602 also may include computer-readable media.

Main memory 604 may contain computer-readable medium (not shown), such as RAM in an example embodiment. An example of main memory 604 includes random access memory (RAM) such as static RAM (SRAM), dynamic RAM (DRAM), non-volatile RAM (NV-RAM), or the like, read only memory (ROM), another type of memory, or a combination thereof. Static memory 606 may contain computer-readable medium (not shown), such as NOR or NAND flash memory in some example embodiments. While the computer-readable medium is shown to be a single medium, the term "computer-readable medium" includes a single-medium or multiple medium, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random-access memory or other volatile re-writable memory. Additionally, the computer-readable medium can include a magneto-optical or optical medium, such as a disk or tapes or other storage device to store information received via carrier wave signals such as a signal communicated over a transmission medium. Furthermore, a computer readable medium can store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

The information handling system 605 may also include the EHRs 632 that may be operably connected to the bus 608. The EHR 632 computer readable medium 622 may also contain space for data storage such as data related to each patient the blood vessel detection system 610 interacts with. During operation the EHR 632 may receive these records from the blood vessel detection system 610 and related to a recorded internal structure of blood vessels within the patient's body as well as other data including date, time, patient ID and VAD used.

In other embodiments, dedicated hardware implementations such as application specific integrated circuits, programmable logic arrays and other hardware devices can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

When referred to as a "system", a "device," a "module," a "controller," or the like, the embodiments described herein can be configured as hardware. For example, a portion of an information handling system device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCM-CIA) card, or other such expansion card), or a system (such as a motherboard, a system-on-a-chip (SoC), or a stand-alone device). The system, device, controller, or module can include software, including firmware embedded at a device, such as an Intel® Core class processor, ARM® brand processors, Qualcomm® Snapdragon processors, or other processors and chipsets, or other such device, or software capable of operating a relevant environment of the information handling system. The system, device, controller, or module can also include a combination of the foregoing examples of hardware or software. In an embodiment an information handling system 605 may include an integrated circuit or a board-level product having portions thereof that can also be any combination of hardware and software. Devices, modules, resources, controllers, or programs that are in communication with one another need not be in continuous communication with each other, unless expressly specified otherwise. In addition, devices, modules, resources, controllers, or programs that are in communication with one another can communicate directly or indirectly through one or more intermediaries.

During operation of the information handling system 605, data may be received at the processor 602 from the blood vessel detection system 610. As described herein the blood vessel detection system 610 may record the internal structures of the patient's body, calculate a trajectory of a VAD to be inserted into the patient's body, provide a VAD recommendation, and provide VAD trajectory feedback, among other operations. These operations and functionalities may be executed using the processor 602 of the information handling system 605, the processor of the blood vessel detection system 610, or a combination of both.

In an embodiment, the processor 602 of the information handling system 605 may be communicatively coupled to the blood vessel detection system 610 via a wireless connection or a wired connection. In these embodiments, the processor 602 may cooperate with the blood vessel detection system 610 so as to provide additional processing resources as well as receive and categorize data descriptive of the patient the blood vessel detection system 610 is being used on, the VAD chosen, and any video associated with that insertion.

Figure 7A:
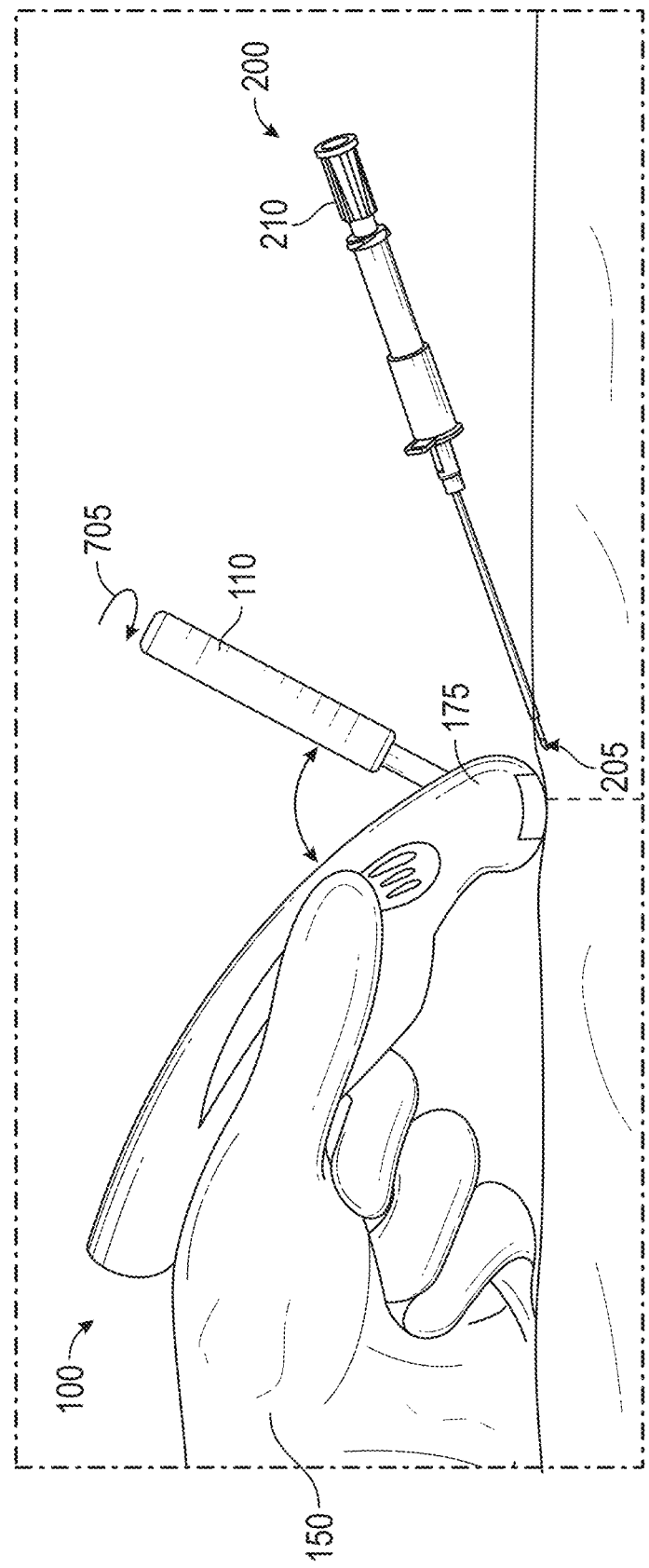
FIG. 7A is side view of an intravenous therapy system 100 interfacing with a patient's arm according to some embodiments of the present disclosure.
Figure 7B:
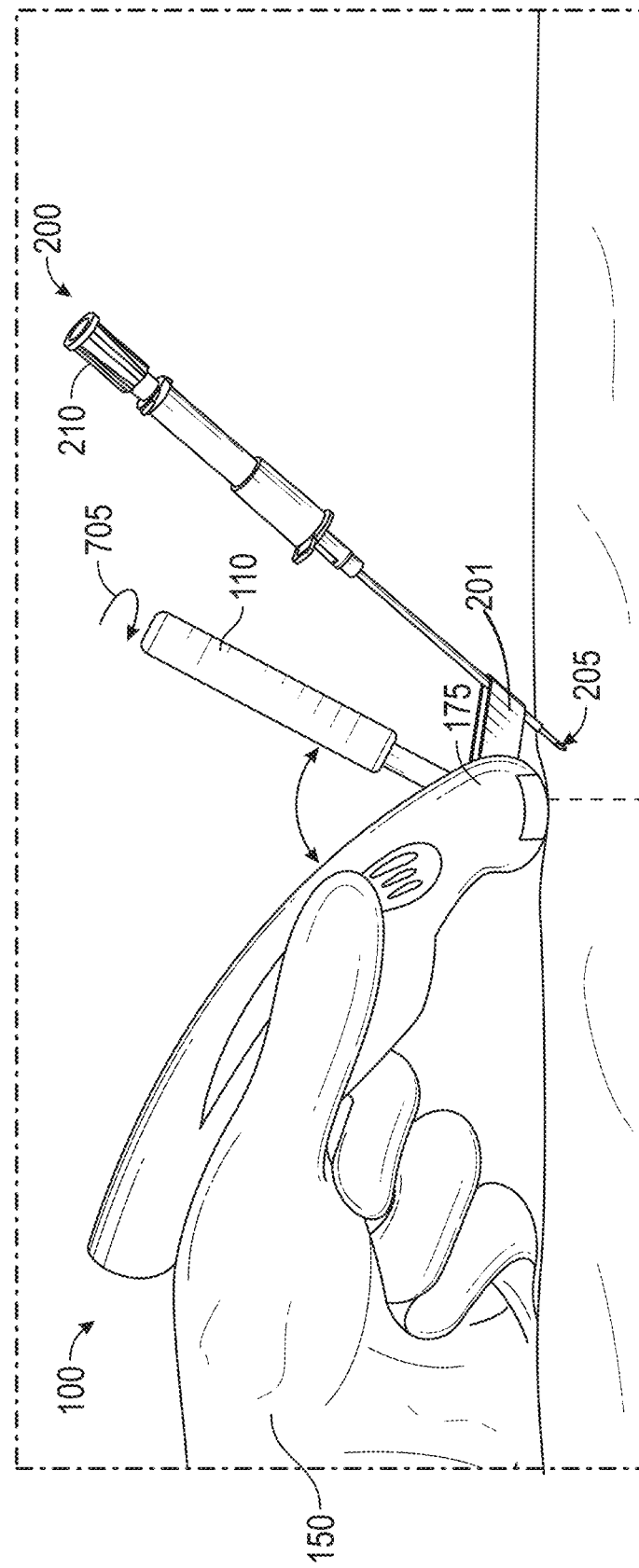
FIG. 7B is side view of an intravenous therapy system 100 interfacing with a patient's arm, illustrating an example drive mechanism for automatic insertion of an example needle, according to some embodiments of the present disclosure.

FIGS. 7A-7B are side views of an intravenous therapy system 100 interfacing with a patient's arm according to some embodiments of the present disclosure. This figure shows the intravenous therapy system 100 being used by a clinician or other HCP with the intravenous therapy system 100 being held in one hand 150 with a VAD 200 being manually inserted into the patient's arm. In this embodiment, the intravenous therapy system 100 may be used with the clinician or other HCP using both hands. Accordingly, the intravenous therapy system 100 includes a video display device 110 housed within the housing of the intravenous therapy system so that the clinician or other HCP may have his or her attention directed toward the location of the blood vessel to be accessed by the VAD 200 instead of off-site towards another video display away from the patient. In order to facilitate the use of the video display device 110 with the clinician or other HCP using both hands, the video display device 110 may be turned around as indicated by the arrow 705. This allows the clinician or other HCP to operate the intravenous therapy system 100 and still see the video display device 110 regardless of the relative orientation of the intravenous therapy system 100 and the VAD 200. In some embodiments, the US probe may include a drive mechanism 201 attached to the US probe, to facilitate automatic insertion of the needle into the blood vessel.

In some embodiments, the drive mechanism 201 may be replaced with a needle guide, attached to the US probe to assist the clinician in manual delivery of the needle at an optimal, predetermined, or desired angle. In some examples, the VAD 200 may be presented at the patient's arm under the intravenous therapy system 100 in order to ensure the trajectory of the VAD 200 is on track to access a blood vessel.

In some embodiments, the drive mechanism 201 may include one or more motors, such as, for example, linear motors or rotational motors or any other suitable type of motors. In some embodiments, the drive mechanism 201 may advance the catheter and/or the needle in the distal direction. In some embodiments, in response to the needle tip entering the vein, the drive mechanism 201 may lower an angle of the VAD with respect to skin of the patient. In some embodiments, the drive mechanism 201 may advance the catheter and then retract the needle in response to the needle tip entering the vein. In some embodiments, the drive mechanism 201 may perform motor-driven pivoting to adjust a position of the VAD.

Figure 8:
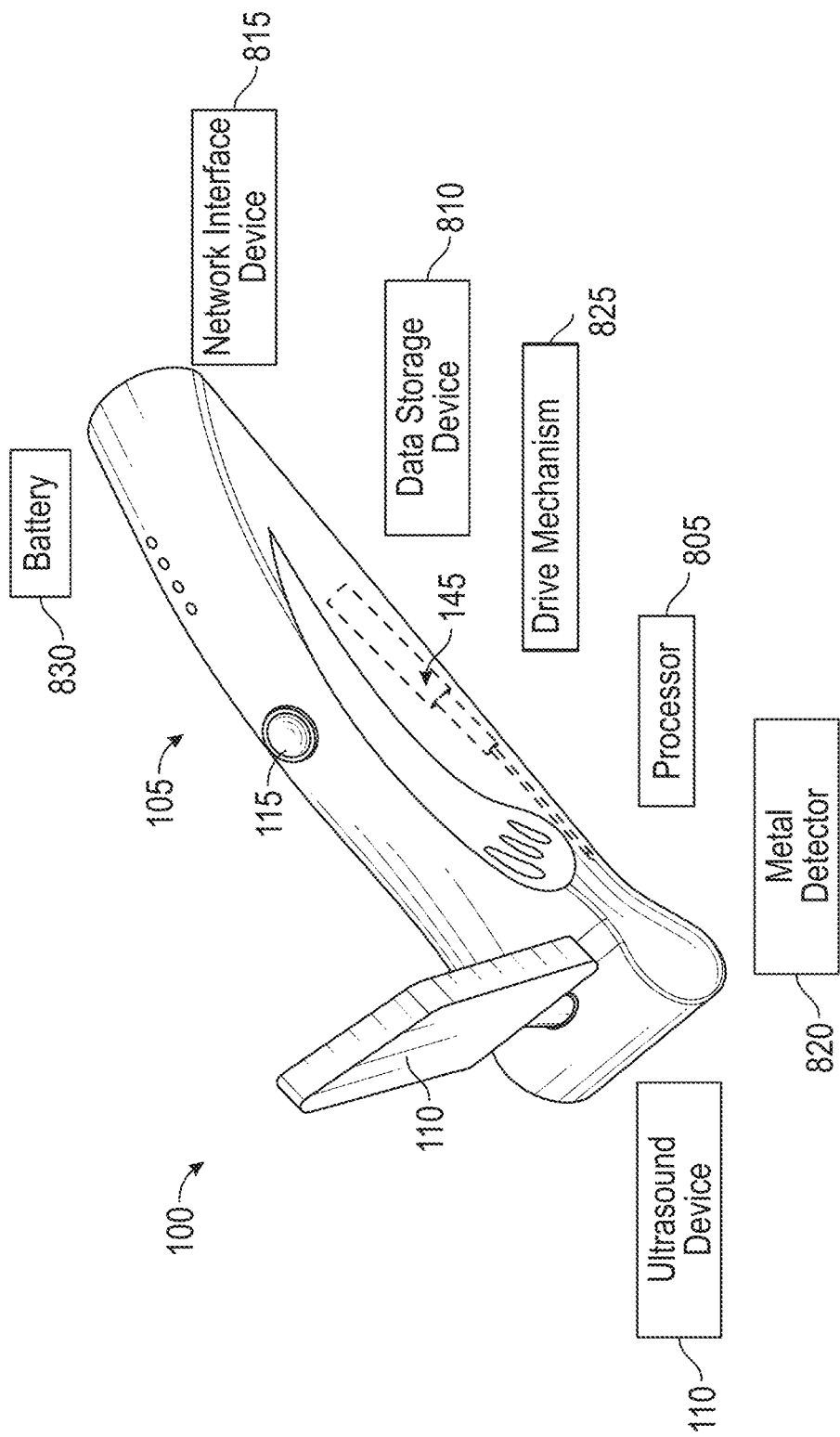
FIG. 8 is a perspective view of an intravenous therapy system 100 according to some embodiments of the present disclosure.

FIG. 8 is a perspective view of an intravenous therapy system 100 according to some embodiments of the present disclosure. As described herein, the housing 105 of the intravenous therapy system 100 may include a plurality of components that allows the intravenous therapy system 100 to operate as a stand-alone device that may or may not be communicatively coupled to a networked information handling system.

The intravenous therapy system 100 may include the VAD chassis 145 as described herein. The VAD chassis 145 may be formed into a portion of the housing 105 that is closest to the patient's body. During operation of the intravenous therapy system 100, in order to allow for the automatic insertion of the VAD into the patient's body, a VAD within the VAD chassis 145 may be automatically advanced into the patient's body. In the embodiments presented herein, the VAD chassis 145 may be communicatively coupled to a processor 805 so as to receive data descriptive of a trajectory the VAD placed within the VAD chassis 145. The data is descriptive of the direction the VAD is to take in order to cause the VAD to intersect with a blood vessel within the patient's body. In these embodiments, the ultrasound (US) device 875 and a magnetic field detector 820 may provide data on a closed-loop feedback in order to direct the VAD into the patient's blood vessel as the VAD engages the patient's skin and the VAD is directed through the patient's body.

In the embodiments herein, the VAD chassis 145 may include a VAD advancement system that includes a drive mechanism 825, which may include one or more linear motors and/or one or more rotational motors. The VAD advancement system may receive signals from the processor 805 as described herein in order to advance the VAD into the patient's body using the drive mechanism 825. In some embodiments presented herein, the drive mechanism 825 may be produce a linear force along its length. This may allow the linear motor 825 to pass the VAD loaded into the VAD chassis 145 away from the housing 105 of the intravenous therapy system 100 and into the body of the patient. In an embodiment, the drive mechanism 825 may also allow for the tilt movement, the rotation movement, and the yaw movement of the VAD during insertion. The linear, tilt, rotational, and taw adjustments of the direction of the VAD allows for the VAD to intersect with the blood vessel of the patient in situations where the intravenous therapy system 100 is moved, either deliberately or accidentally, along the surface of the patient's body.

In some embodiments, the drive mechanism 825 may advance the catheter and/or the needle in the distal direction. In some embodiments, in response to the needle tip entering the vein, the drive mechanism 825 may lower an angle of the VAD with respect to skin of the patient. In some embodiments, the drive mechanism 825 may advance the catheter and then retract the needle in response to the needle tip entering the vein. In some embodiments, the drive mechanism 825 may be substituted for one or more drive mechanisms of any suitable kind.

The intravenous therapy system 100 also includes a video display device 110 communicatively coupled to the US device 875 and the processor 805 within the housing 105 among other components of the intravenous therapy system 100. In an embodiment, the video display device 110 may receive input from the processor 805 descriptive of the data received by the US device 875. This input from the processor 805 causes images of the structures within the patient's body to be presented on the video display device 110. The images presented may change as the position of the US device 875 placed against the patient's body changes. In an embodiment, the data from the US device 875 sent to the processor 805 may be data descriptive of a transverse view of the structures of a blood vessel such as a vein within a patient's arm that are on a transverse plane of the arm. In any embodiment presented herein, however, it is understood that the US device 875 may be placed against any portion of the patient's body such as a leg in order to locate and access a blood vessel with a VAD. In an embodiment, the data from the US device 875 sent to the processor 805 may be data descriptive of a coronal view of the structures such as a vein within a patient's arm that are on a coronal plane of the arm. The view along the coronal plane may be a longitudinal view of a blood vessel of the patient that runs the length of the patient's arm. The video display device 110 may display either or both of the coronal planar view along the coronal plane of the patient, the transverse planar view along the transverse plane of the patient, or both as described herein.

The intravenous therapy system 100 may also include a data storage device 810. The data storage device 810 may receive data from the US device 875, the magnetic field detector 820, and the video display device 110. This data may include, among other data, patient identification data, VAD identification data, magnetic field detector and ultrasound data, time data, date data, and anatomy geometries.

In order to operate in a stand-alone configuration, the housing 105 of the intravenous therapy system 100 may include a battery 830. The battery 830 may include, in some embodiments, a smart battery system or be operatively coupled to a power management unit that tracks and provides power state data. This power state data may be stored with the instructions, parameters, and profiles to be used with the intravenous therapy system 100 and stored on the data storage device 810.

Figure 9:
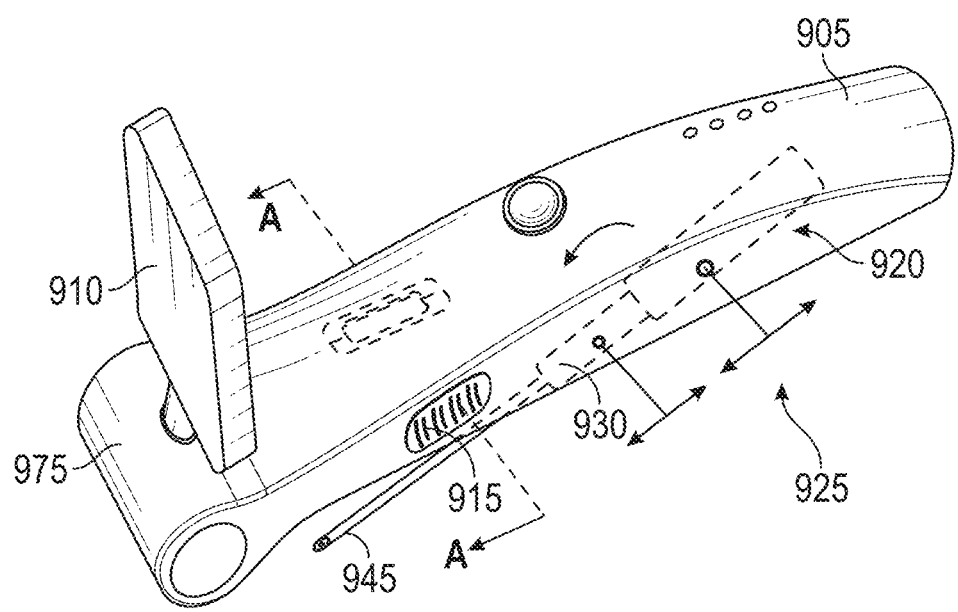
FIG. 9 is a perspective view of an intravenous therapy system according to an embodiment of the present disclosure.

FIG. 9 is a perspective view of an intravenous therapy system 900 according to an embodiment of the present disclosure. The intravenous therapy system 900, similar to other embodiments, includes a video display device 910 to display a view of the internal structures of a patient's body and a US probe 975 used to detect those internal structures. In an embodiment, the intravenous therapy system 900 may further include one or more VAD advancement buttons 915 used to automatically advance a VAD into and through the patient's body as well as, pivot, rotate and or retract the VAD or a portion of the VAD. The VAD advancement buttons 915 may be any type of actuation device that allows a clinician or other HCP to selectively engage a linear motor or another type of motor so that the linear motor 925 may advance a VAD out from a VAD chassis 945 and into the body of a patient. In a specific example, the VAD advancement buttons 915 may be oriented on a first and second side of the housing 905 of the intravenous therapy system 900 so as to accommodate for both right-handed and left-handed clinicians or other HCPs that may use the intravenous therapy system 900. In a specific embodiment, the VAD advancement buttons 915 may allow for relatively fast or slow insertion of the VAD into the patient's body based on how far along the surface of the housing 905 the clinician or other HCP advances the VAD advancement buttons 915. For example, if the VAD advancement buttons 915 is advanced by the clinician or other HCP along the housing 905 for 1 mm, the VAD may move at a slower rate than if the clinician or other HCP advances the VAD advancement buttons 915 for 2 mm along the surface of the housing 905. In this manner, a clinician or other HCP may control the speed at which the VAD is advanced into the patient's body so that those less familiar with the operations of the intravenous therapy system 900 may learn how to use the intravenous therapy system 900 without hurting the patient and while still accomplishing the task of VAD insertion into the patient's blood vessel.

In alternative embodiments, the advancement buttons 915 may individually control the depth into which the VAD is advanced into the patient's body and the direction into which the VAD is advanced into the patient's body. For example, a first of the plurality of advancement buttons 915 may, when pulled back towards a proximal end of the intravenous therapy system 900 cause a distal end of the VAD to point upward in the positive z-direction while pushing the first of the plurality of advancement buttons 915 causes the distal end of the VAD to point downward in the negative z-direction. With the video display device 910 the clinician or other HCP may use the first of the VAD advancement buttons 915 to follow a determined trajectory of the VAD while also receiving input from the video display device 910 as to whether the clinician or other HCP is directing the VAD along the z-direction to follow the trajectory.

In this alternative embodiment, the second of the plurality of VAD advancement buttons 915 may be used to control the x- or y-directional trajectory of the VAD. Again, movement of the second of the plurality of VAD advancement buttons 915 in a forward direction may direct the distal tip of the VAD in the positive x-direction while pulling the second of the plurality of VAD advancement buttons 915 causes the distal tip of the VAD in the negative x-direction. A third of the plurality of VAD advancement buttons 915 may be similarly used to advance the distal tip of the VAD in the positive y and negative y-direction.

The intravenous therapy system 900 may, in some embodiments, include a plurality of motors, which may include linear motors and/or rotational motors. In the embodiment presented herein, the intravenous therapy system 900 includes a driving linear motor 920, a retracting linear motor 925, and a rotational motor 930. Each of these motors 920, 925, 930 may be activated automatically to drive the VAD 945 into the patient's body. The driving linear motor 920 may drive the VAD 945 from the intravenous therapy system 900. The retracting linear motor 925 may drive the VAD 945 back and into the VAD chassis formed in the housing 905 of the intravenous therapy system 900. The rotational motor 930 may change the rotational direction of the VAD 945 and, in an embodiment, change the pitch and yaw of the VAD 945 as the driving linear motor 920 pushes the VAD 945 into the body of the patient.

Figure 10:
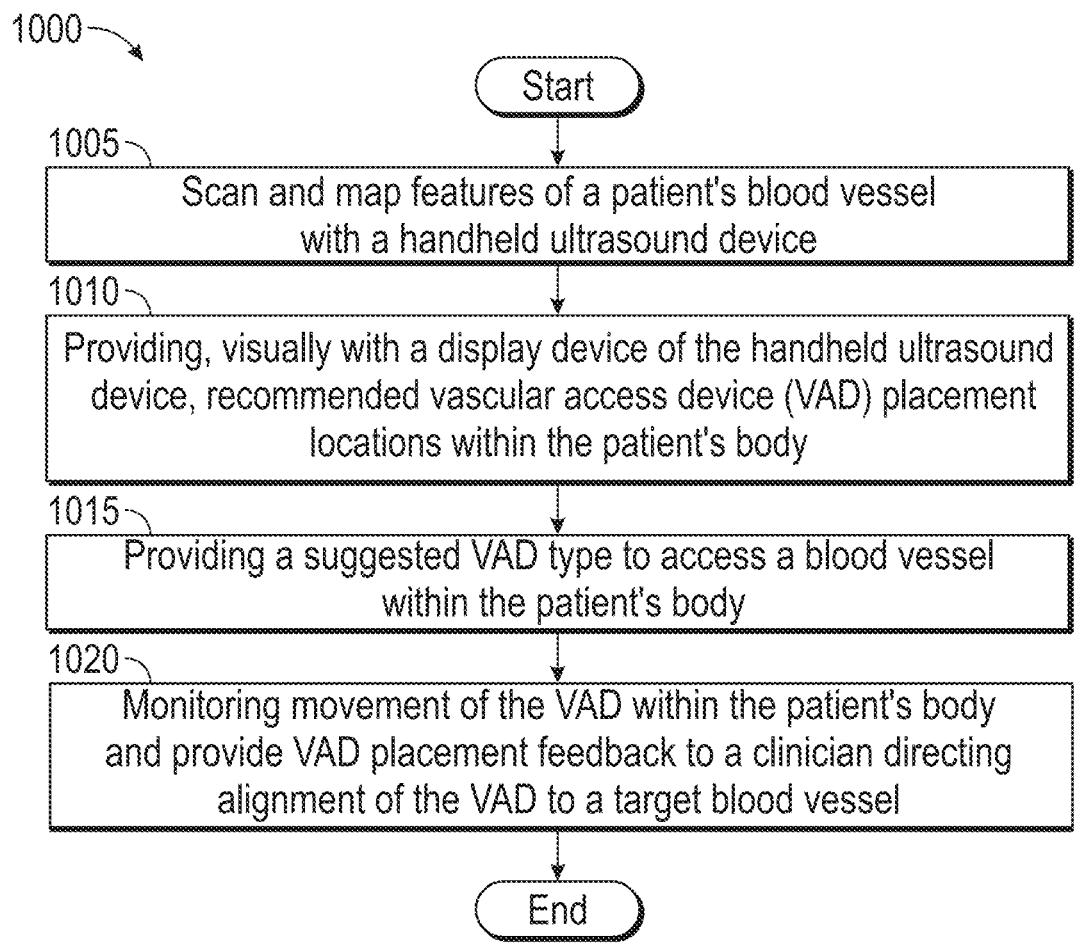
FIG. 10 is a flowchart depicting a method of operating an intravenous therapy system according to some embodiments of the present disclosure.

FIG. 10 is a flowchart depicting a method 1000 of operating an intravenous therapy system according to some embodiments of the present disclosure. The method 1000 may include, at block 1005, scanning and mapping features of a patient's blood vessel with a handheld ultrasound device. As descried herein, the handheld ultrasound device may include an ultrasound device that detects the structures within a patient's body along a plurality of planes including a transverses plane and a coronal plane as described herein. The ultrasound device may be communicatively and operatively coupled to a processor that receives the data from the ultrasound device.

The method 1000 may also include providing, visually with a display device of the handheld ultrasound device, recommended VAD placement locations within the patient's body at block 1010. As described herein, the data received by the processor may be used to detect the presence of a blood vessel such as a vein within the patient's body. In an embodiment, the processor may determine a location of a blood vessel based on a detection of blood flow from the ultrasound device, the differences in hues of colors presented on the display device of the interior structures of the patient's body, the detection of movement of the exterior walls of the blood vessel, among other types of indicia.

The method 1000 may further include, at block 1015, providing a suggested VAD type to access a blood vessel within the patient's body. The type of VAD recommended by the, in an example a VAD recommendation module, may be dependent on a number of factors including the location of the blood vessel to be accessed, the type, condition and anatomy of the blood vessel being accessed, the purpose of the VAD (e.g., blood sampling or infusion therapies), and patient characteristics, among other factors. The type of VAD recommended may include specifics about a VAD such as length, gauge, and material, among other features of a VAD. As described herein in an embodiment, the suggested VAD type may be provided on a video display device after execution of a VAD recommendation module by the processor of the intravenous therapy system. During operation, a clinician or other HCP may review the VAD recommendation, locate the recommend VAD, and load the VAD into a VAD chassis of the intravenous therapy system for later insertion into the patient.

The method 1000 may further include monitoring movement of the VAD within the patient's body and provide VAD placement feedback to a clinician directing alignment of the VAD to a target blood vessel at block 1020. As described herein, the intravenous therapy system may include both an ultrasound (US) device and a magnetic field detector. The data received from the US device and the magnetic field detector may be provided to the processor in order to determine the relative location of the tip of the VAD to the VAD placement location determined previously by the processor. In an embodiment, the processor may overlay an image of the VAD onto US images presented on the video display device so that a clinician or other HCP may see the trajectory of the VAD as it passes through the patient's body and into the blood vessel. In an embodiment, the movement of the VAD may be accomplished by the clinician or other HCP. In another embodiment, the movement of the VAD may be automatic via use of one or more linear motors formed within a VAD chassis. In any embodiment presented herein, the clinician or other HCP may select between a manual VAD insertion mode or an automatic VAD insertion mode. Upon selection of the manual VAD insertion mode, the clinician may be provided with a VAD recommendation and initiate a manual insertion of the VAD as described herein. Upon selection of an automatic VAD insertion mode, the clinician may be provided with a VAD recommendation, insert the VAD into the VAD chassis, and initiate the automatic insertion of the VAD into the patient's body as described herein. During operation of the automatic VAD insertion mode the processor may pause the automatic insertion of the VAD if and when it is detected that the VAD is not following a calculated trajectory. Similarly, the clinician may initiate a manual override for any of a number of reasons including, but not limited to, clinician error and nonessential use of the VAD.

Figure 11:
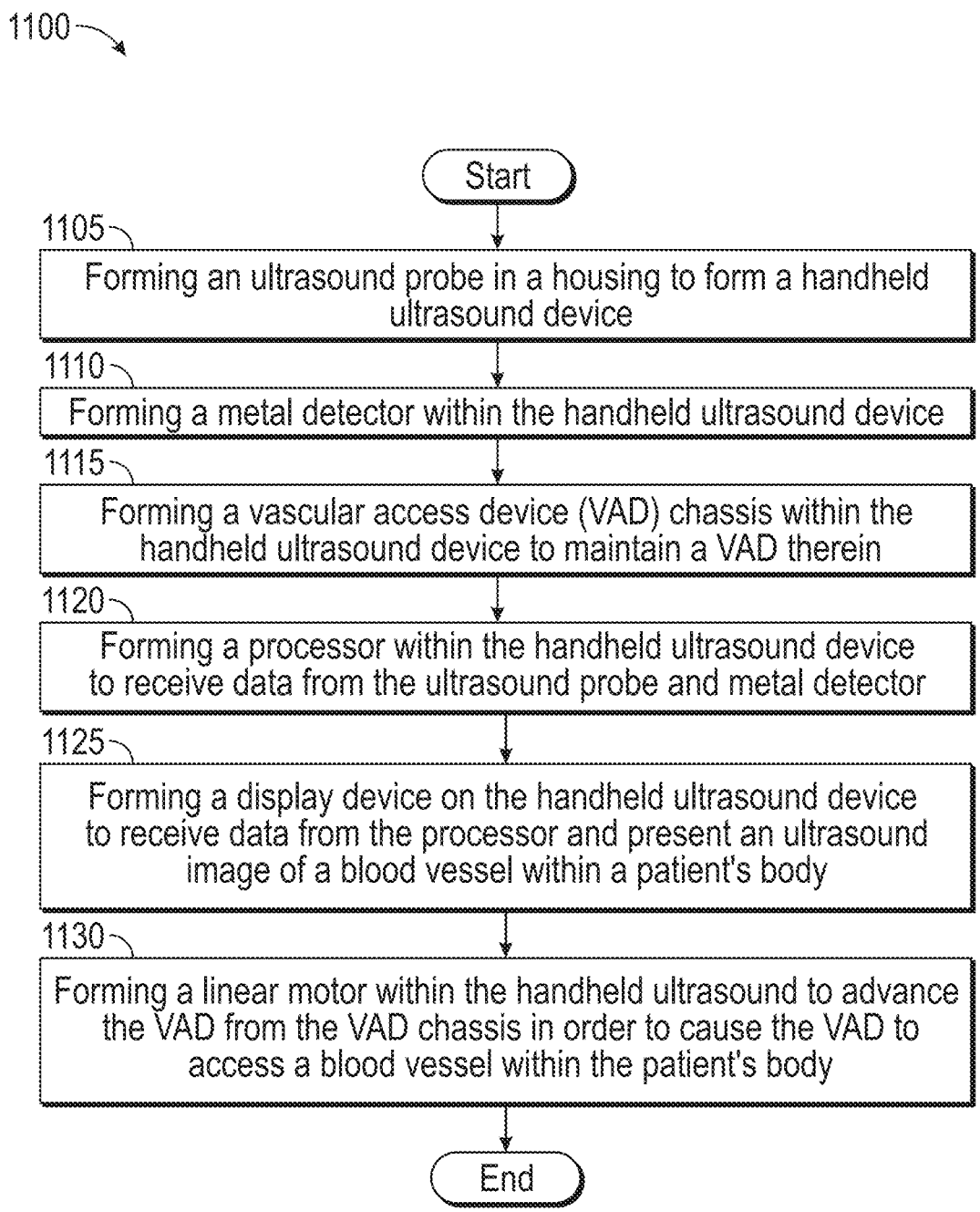
FIG. 11 is a flowchart depicting a method of manufacturing an intravenous therapy system according to some embodiments of the present disclosure.

FIG. 11 is a flowchart depicting a method 1100 of manufacturing an intravenous therapy system according to some embodiments of the present disclosure. The method 1100 may include forming, at block 1105, an ultrasound (US) probe in a housing to form a handheld US device. In an embodiment the housing may be made of a plastic or other non-metallic material so as to avoid interference with the US probe and a magnetic field detector within the intravenous therapy system. The US probe may be any device that converts electrical signals from an electrical source into ultrasound waves and converts ultrasound waves received at the US probe into electrical signals. During operation of the US probe, the US probe may receive an electrical signal and convert that electrical signal into ultrasound waves that are directed, either continuously or pulsed, to enter into a part of a patient's body. As the ultrasound waves enter the patient's body, those ultrasound waves may be reflected off of structures within the patient's body and reflected back to the US probe. When the reflected ultrasound waves reach the US probe within a window of time, sometimes corresponding to a time it takes for the energy to pass through a depth of the patient's body, the US probe converts those ultrasound waves back into electrical signals. These electrical signals may be interpreted by a processor housed within the housing of the intravenous therapy system and used to form an image of the internal structures within the patient's body. In an embodiment presented herein, the electrical signals presented to the processor and used to form the images of the structures within the patient's body may be displayed at a video display device of the intravenous therapy system. In a specific application and during operation of the intravenous therapy system, the US probe may be directed towards an arm of the patient in order to detect a position of a blood vessel within the patient's arm.

The method 1100 may further include forming a magnetic field detector within the handheld ultrasound device at block 1110. The magnetic field detector may detect any metal components of a VAD to be inserted into the patient. In an embodiment, the magnetic field detector may detect the location of the metal components of the VAD relative to the US probe. In these embodiments, the processor of the intravenous therapy system may overlay positional location data related to the location of the metal components of the VAD onto any images presented on a video display device.

By way of example, when the video display device displays a coronal plane of the patient's arm, the video display device may show the movement of the VAD passing into the blood vessel. Similarly, when the video display device displays a transverse plane of the patient's arm, the video display device may show a trajectory point to which the VAD is going to intersect with the blood vessel.

The method 1100 may include, at block 1115, includes forming a vascular access device (VAD) chassis within the handheld US device to maintain a VAD therein. As described herein, the VAD chassis may hold any type of VAD therein during operation of the intravenous therapy system.

The method 1100 may also include, at block 1120, forming a processor within the handheld US device to receive data from the ultrasound probe and magnetic field detector. The processor may be communicatively coupled to the US probe, the magnetic field detector, and a linear motor, among other devices housed within the housing of the ultrasound device described herein. As described herein, the data received by the processor from the magnetic field detector and US probe may be used to display the movement of the VAD through the patient's body on the video display device.

The method 1100 may further include forming a display device on the handheld ultrasound device to receive data from the processor and present an ultrasound image of a blood vessel within a patient's body at block 1125. In the embodiments described herein, the data produced at the video display device may be used by the clinician or other HCP to manually or automatically direct the VAD into the patient's body. Because the video display device is formed into the housing of the intravenous therapy system, the clinician or other HCP may keep their line of sight at the location where the VAD is being inserted into the patient's body so that the clinician or other HCP may, in real time, monitor the advancement of the VAD into and through the patient's body. In other embodiments, the video display device may be used to assess proper initial placement of the VAD, and any provide subsequent indwelling assessments of the VAD within the patient's body.

The method 1100 may also include, at block 1130, forming a linear motor within the handheld ultrasound to advance the VAD from the VAD chassis in order to cause the VAD to access a blood vessel within the patient's body. As described herein, a plurality of linear and/or rotational motors may be used to align the VAD along a determined trajectory the VAD is to follow so that the VAD may intersect with an identified blood vessel within the patient's body. As such, these motors may control the VAD so as to orient or rotate the VAD in any direction along any x-, y-, or z-coordinate plane. During implementation of the intravenous therapy system described herein, the processor may have created a trajectory path through the patient's body leading from a distal tip of the VAD to a predetermined location within a blood vessel. The processor, through actuation of a VAD advancement button by a clinician or other HCP, may direct the linear motors to pass the distal tip of the VAD along this path and into the blood vessel of the patient. In other embodiments, the clinician may manually pass the VAD through the patient's body based on the created trajectory with the processor providing visual, haptic, or audible alerts to the clinician or other HCP when the trajectory is not being followed. Consequently, the method 1100 may further include the forming of a speaker and/or haptic feedback device into the housing of the intravenous therapy system.

In an embodiment, the method 1100 may further include forming a battery and data storage device within the housing of the intravenous therapy system. The battery may provide power to the different devices within the intravenous therapy system while the data storage device maintains data and computer readable program code to be accessed by the processor during operation of the intravenous therapy system.

The embodiments described herein provide for an intravenous therapy system that includes a visual display device used to direct a VAD into the body of a patient in order to properly and easily access a blood vessel therein. These embodiments implement an US device that detects the internal structure of the patient's body and displays images of those internal structures, such as blood vessels, on a display device physically and operatively coupled to the housing of the US device. During manual insertion of a VAD into the patient's body, a clinician or other health care provider may detect where the distal tip of the VAD is relative to a target location within the blood vessel via use of a magnetic field detector housed within the US device. The metal tip of the VAD may be overlaid onto the US images presented at the video display device so that the user may more easily recognize how to orient the VAD during insertion. Additionally, a trajectory may be calculated by a processor of the US device such that the manual insertion of the VAD may be monitored and alters may be presented to the clinician or other HCP if and when the current trajectory of the VAD is off target from the calculated trajectory. This allows for accurate and precise placement of the VAD into the patient's body resulting in less damage the tissue of the patient's body and less anxiety experienced by the patient.

In an additional embodiment, the VAD may be more accurate inserted into the patient's body through the use of a VAD chassis and linear motors. The VAD chassis may be used to hold a VAD that has been recommended to the clinician or other HCP after the processor has received data from the US device as well as other data related to the patient and purpose of the VAD. Upon coupling of the VAD into the VAD chassis, the intravenous therapy system may actuate any number of linear motors that control the alignment of the VAD to a trajectory calculated by the processor. Thus, in this embodiment, the clinician or other HCP may maintain the intravenous therapy system at a location on the patient's arm while the automatic VAD placement systems place the VAD into and through the patient's body along the recommended trajectory. Again, if the intravenous therapy system is moved, an alert system may indicate to the clinician that the intravenous therapy system is to be returned to the appropriate position so that the VAD may be advanced appropriately. Because the video display device presents real-time images of the internal structures of the patient's body as well as the location of the VAD within the body, a clinician may better assess the trajectory of the VAD at any time. Thus, the intravenous therapy system provides a continual feedback loop so as to more accurately and precisely locate the VAD within a blood vessel.

With the use of a US device within the intravenous therapy system, a video recording may be generated and saved on a memory device interior or remote to the intravenous therapy system so that an EHR may be maintained descriptive of the VAD being used, the data and time of the insertion of the VAD, any patient data, and intended uses of the VAD. This may create a more robust record of care related to any given patient thereby increasing the efficiency of any medical treatment provided. These records may be maintained on a central database when the intravenous therapy system transfers the data to an information handling system or other computing device via a wired or wireless connection.

Again, it is understood that the embodiments of the present application may be combined. As an example, the embodiments of FIGS. 1-9 may be arranged to fit specific uses based on the type of action being conducted. For example, where an artery is to be accessed by the VAD, the intravenous therapy system may indicate, via the indicator system, a location of the artery while avoiding any veins. This may allow for the introduction of certain medicaments into a specific location in the patient's body without concern for that medicament being distributed throughout the patient's body. Similarly, arteries may be avoided when a vein is to be accessed.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous therapy system, comprising:
   a stand-alone device, comprising:
      a processor;
      a data storage device; and
      a housing comprising a distal end coupled to an ultrasound probe to detect a blood vessel within a patient's body;
      a video display device extending from the housing and operatively coupled to the ultrasound probe, wherein the video display device is configured to display the blood vessel detected by the ultrasound probe and a trajectory indicator; and
      a magnetic field detector configured to determine a position of a needle of a vascular access device (VAD) and provide data on a closed-loop feedback, wherein the processor is configured to calculate a trajectory of the VAD based on the data from the closed-loop feedback from the magnetic field detector, wherein the trajectory indicator indicates whether the VAD is in line with the trajectory as the VAD passes through the patient's body during operation of the ultrasound probe;
   a VAD chassis formed within a bottom of the housing and communicatively coupled to the processor, wherein the processor is configured to receive the data from the closed-loop feedback when the VAD is loaded within the VAD chassis; and
   a linear motor configured to automatically advance the VAD, when the VAD is loaded in the VAD chassis, into the patient's body along the trajectory, wherein the trajectory does not intersect with the ultrasound probe at the distal end of the housing.

2. The intravenous therapy system of claim 1, wherein the video display device is configured to display a vein via a transverse planar image of the blood vessel within the patient's body.

3. The intravenous therapy system of claim 1, further comprising a VAD recommendation module to provide feedback, via the video display device, a recommendation of which of a plurality of different VADs are to be used to access the blood vessel.

4. The intravenous therapy system of claim 1, wherein the video display device provides a coronal planar view of the blood vessel within the patient's body depicting a projected path of the needle within the patient's body and a transverse planar view depicting the projected path of the needle within the patient's body.

5. The intravenous therapy system of claim 1, wherein the processor is housed within the housing.

6. The intravenous therapy system of claim 1, wherein the processor causes a projected path of the VAD to be overlaid onto ultrasonic images on the video display device during operation of the ultrasound probe.

7. The intravenous therapy system of claim 1, wherein the housing comprises a button, wherein the button is configured to be actuated to automatically advance the needle along the trajectory via the linear motor in response to the trajectory of the needle being within the blood vessel detected by the ultrasound probe.

8. The intravenous therapy system of claim 7, wherein actuation of the button is configured to be overridden in response to the trajectory not intersecting the blood vessel detected by the ultrasound probe.

9. The intravenous therapy system of claim 8, further comprising an audio feedback device, a haptic feedback device, or a visual feedback device to indicate a projected path is not intersecting the blood vessel detected by the ultrasound probe.

10. The intravenous therapy system of claim 1, wherein the trajectory indicator indicates a depth of the VAD, wherein the trajectory indicator is color coded to indicate whether the depth of the VAD is in line with the trajectory.

11. The intravenous therapy system of claim 1, wherein the trajectory indicator indicates x- and y-coordinates of the VAD, wherein the trajectory indicator is color coded to indicate whether placement of the VAD is in line with the trajectory.

* * * * *